United States Patent
Quinlan

(10) Patent No.: US 10,500,524 B2
(45) Date of Patent: Dec. 10, 2019

(54) SEPARATION SYSTEMS AND METHODS OF USING THEM

(71) Applicant: George L Quinlan, Bassett, VA (US)

(72) Inventor: George L Quinlan, Bassett, VA (US)

(73) Assignee: Quinlan Properties, LLC, Bassett, VA (US)

( * ) Notice: Subject to any disclaimer, the term of this patent is extended or adjusted under 35 U.S.C. 154(b) by 224 days.

(21) Appl. No.: 15/469,990

(22) Filed: Mar. 27, 2017

(65) Prior Publication Data

US 2018/0043279 A1    Feb. 15, 2018

Related U.S. Application Data

(63) Continuation of application No. 13/954,248, filed on Jul. 30, 2013, now Pat. No. 9,604,153.

(60) Provisional application No. 61/677,803, filed on Jul. 31, 2012.

(51) Int. Cl.

| | |
|---|---|
| *B01D 3/40* | (2006.01) |
| *B01D 3/36* | (2006.01) |
| *B01D 3/14* | (2006.01) |
| *B01D 3/26* | (2006.01) |
| *B01D 11/04* | (2006.01) |
| *H01L 21/02* | (2006.01) |
| *B01D 11/02* | (2006.01) |
| *B01D 3/30* | (2006.01) |
| *C07C 45/82* | (2006.01) |
| *C07C 49/395* | (2006.01) |
| *B01D 3/16* | (2006.01) |
| *B01J 3/00* | (2006.01) |

(52) U.S. Cl.
CPC ............... *B01D 3/40* (2013.01); *B01D 3/36* (2013.01); *B01D 11/0203* (2013.01); *B01D 11/0403* (2013.01); *B01D 11/0407* (2013.01); *H01L 21/02101* (2013.01); *B01D 3/14* (2013.01); *B01D 3/16* (2013.01); *B01D 3/26* (2013.01); *B01D 3/30* (2013.01); *B01J 3/008* (2013.01); *C07C 45/82* (2013.01); *C07C 49/395* (2013.01)

(58) Field of Classification Search
USPC ............... 202/176; 210/666, 674, 198.2
See application file for complete search history.

(56) References Cited

U.S. PATENT DOCUMENTS

| | | | |
|---|---|---|---|
| 5,160,414 A * | 11/1992 | Lee | B01D 3/40 203/57 |
| 2004/0020518 A1* | 2/2004 | DeYoung | B08B 7/0021 134/30 |
| 2006/0124552 A1* | 6/2006 | Nagai | B01D 19/0068 210/689 |
| 2006/0226117 A1* | 10/2006 | Bertram | H01L 21/02057 216/59 |

\* cited by examiner

*Primary Examiner* — Benjamin R Whatley
*Assistant Examiner* — Brittany I Fisher
(74) *Attorney, Agent, or Firm* — Rhodes IP PLC; Christopher R Rhodes

(57) ABSTRACT

Certain embodiments described herein are directed to separation systems and methods effective to separate two or more solvents in a solvent mixture. In certain examples, a system effective to separate two or more azeotrope forming solvents is provided. In some embodiments, the system can be effective to remove at least about 95% of one of the solvents from the solvent mixture.

15 Claims, 9 Drawing Sheets

SEPARATION SYSTEMS AND METHODS OF USING THEM

PRIORITY APPLICATION

This application claims the benefit of, and priority to, U.S. Application No. 61/677,803 filed on Jul. 31, 2012, the entire disclosure of which is hereby incorporated herein by reference.

TECHNOLOGICAL FIELD

Certain features, aspects and embodiments are directed to separation systems and methods of using them. In certain embodiments, a separation system can be used to separate two or more azeotropic forming solvents in a solvent mixture.

BACKGROUND

Distillation is commonly used to separate solvents from each other by using the differences in boiling points of the solvents. Where the boiling points of the solvents are close to each other or where the solvents form azeotropes with each other, multiple distillation steps may be required, which takes substantial time and results in substantial costs.

SUMMARY

In a first aspect, a system comprising a chamber configured to receive a solvent mixture, a pump fluidically coupled to the chamber at a first port of the chamber and configured to provide a supercritical fluid stream at an effective temperature and pressure to the solvent mixture in the chamber to remove a selected amount by weight or volume, e.g., at least about 25%, at least about 50% or at least about 75% by weight or by volume, based on the total weight of the solvent mixture or the total volume of the solvent mixture respectively, of one solvent from the solvent mixture, and a collection vessel fluidically coupled to a second port of the chamber and configured to receive the removed solvent in the supercritical fluid stream exiting the second port of the chamber is provided. In some embodiments, at least about 80%, 85%, 90%, 95%, 97%, 98% or 99% by weight or by volume of the one solvent is removed from the solvent mixture. In certain embodiments, the amount removed may be removed with a single charge of the supercritical fluid stream, e.g., with a fixed introduced volume of supercritical fluid.

In an additional aspect, an industrial scale system configured to remove a first solvent from an azeotropic solvent mixture in a selected amount, e.g., at least about 25%, at least about 50%, or at least about 75%, by weight or by volume, based on the total weight of the solvent mixture or the total volume of the solvent mixture respectively is described. In certain embodiments, the system comprises a first inlet configured to fluidically couple to a fluid container configured to hold at least 100 liters or more of a fluid comprising the solvent mixture, a chamber comprising a first port configured to be fluidically coupled to the first inlet and configured to receive the fluid from the fluid container, a first pump fluidically coupled to the first port of the chamber and configured to provide the fluid from the fluid container to the chamber, a second pump fluidically coupled to the chamber and configured to provide a supercritical fluid stream to fluid in the chamber at an effective pressure and temperature to remove the selected amount, e.g., e.g., at least about 25%, at least about 50%, or at least 75% by weight or volume, of the first solvent, based on the total weight of the solvent mixture, from the fluid using the supercritical fluid stream, and a collection vessel fluidically coupled to a second port on the chamber and configured to receive the supercritical fluid stream exiting the second port of the chamber to collect the removed, first solvent in the exiting supercritical fluid stream. In some embodiments, at least about 80%, 85%, 90%, 95%, 97%, 98% or 99% by weight or by volume of the first solvent is removed from the solvent mixture.

In another aspect, a portable system configured to remove a first solvent from an azeotropic solvent mixture in a selected amount, e.g., at least about 25%, at least about 50%, or at least 75%, by weight or by volume, based on the total weight of the solvent mixture or the total volume of the solvent mixture respectively, is provided. In certain embodiments, the portable system comprises a DC power source, a chamber configured to receive the azeotropic solvent mixture, a pump electrically coupled to the DC power source and configured to provide a supercritical fluid stream at an effective temperature and pressure to the solvent mixture in the chamber to remove at least the selected amount, e.g., at least about 25%, at least about 50%, or at least 75%, by weight or by volume, based on the total weight of the solvent mixture or the total volume of the solvent mixture, respectively, of the first solvent from the solvent mixture, and a collection vessel fluidically coupled to a second port of the chamber and configured to receive the removed solvent in the supercritical fluid stream exiting the second port of the chamber. In certain embodiments, at least about 80%, 85%, 90%, 95%, 97%, 98% or 99% by weight or by volume of the one solvent is removed from the solvent mixture. In certain embodiments, the amount removed may be removed with a single charge of the supercritical fluid stream, e.g., with a fixed introduced volume of supercritical fluid.

In an additional aspect, an in-line solvent purification system configured to remove at least a selected amount, e.g., at least about 25%, at least about 50%, or at least 75% by weight, by weight or by volume, based on the total weight of the solvent mixture or the total volume of the solvent mixture respectively, of at least one solvent from an azeotropic solvent mixture is disclosed. In certain embodiments, the in-line solvent purification system comprises a first port configured to couple to a processing solvent stream exiting a reactor, a chamber fluidically coupled to the first port to receive an azeotropic solvent mixture in the processing solvent stream, a pump fluidically coupled to the chamber and configured to provide a supercritical fluid stream at an effective temperature and pressure to the azeotropic solvent mixture in the chamber to remove at least the selected amount, e.g., at least about 25%, at least about 50%, or at least 75%, by weight or by volume, based on the total weight of the solvent mixture or the total volume of the solvent mixture respectively, of a first solvent from the azeotropic solvent mixture, a collection vessel fluidically coupled to a second port of the chamber and configured to receive the removed solvent in the supercritical fluid stream exiting the second port of the chamber, and a fluid line fluidically coupled to the collection vessel and configured to provide the removed solvent to the reactor. In some embodiments, at least about 80%, 85%, 90%, 95%, 97%, 98% or 99% by weight or by volume of the one solvent is removed from the solvent mixture. In certain embodiments, the amount removed may be removed with a single charge of the supercritical fluid stream, e.g., with a fixed introduced volume of supercritical fluid.

In another aspect, a system configured to separate at least a selected amount, e.g., at least about 25%, at least about 50%, or at least 75%, by weight or by volume of NMP, based on the total weight of a solvent mixture or the total volume of the solvent mixture respectively, from the solvent mixture comprising NMP and a di-ol is provided. In certain embodiments, the system comprises a chamber configured to receive the solvent mixture and configured for temperature control to maintain the solvent mixture at a selected temperature, a pump fluidically coupled to the chamber at a first port of the chamber and configured to fluidically couple, at a second port of the pump, to a fluid source effective to provide a supercritical fluid stream, the pump configured to provide the supercritical fluid stream at an effective temperature and pressure to the solvent mixture in the chamber to remove at least the selected amount, e.g., at least about 25%, at least about 50%, or at least 75%, by weight or by volume of the NMP, based on the total weight of the solvent mixture or the total volume of the solvent mixture respectively, from the solvent mixture, a collection vessel fluidically coupled to a second port of the chamber and configured to receive the removed NMP in the supercritical fluid stream exiting the second port of the chamber, and a pressure reduction device between the chamber and the collection vessel, the pressure reduction device configured to reduce the pressure of the supercritical fluid stream to permit collection of the NMP, e.g., as a liquid or solid if desired, in the collection vessel. In some embodiments, at least about 80%, 85%, 90%, 95%, 97%, 98% or 99% by weight or by volume of the NMP is removed from the solvent mixture. In certain embodiments, the amount of NMP removed may be removed with a single charge of the supercritical fluid stream, e.g., with a fixed introduced volume of supercritical fluid.

In an additional aspect, a method of removing a solvent from an azeotropic forming solvent mixture comprising a first solvent and a second solvent, the method comprising providing an effective amount of a supercritical fluid stream to the azeotropic solvent mixture to remove a selected amount, e.g., at least about 25%, at least about 50%, or at least 75%, by weight or by volume of the first solvent, based on the total weight of the azeotropic forming solvent mixture or the total volume of the azeotropic forming solvent mixture respectively, from the azeotropic forming solvent mixture is provided. In some embodiments, at least about 80%, 85%, 90%, 95%, 97%, 98% or 99% by weight or by volume of the one solvent is removed from the solvent mixture. In certain embodiments, the amount removed may be removed with a single charge of the supercritical fluid stream, e.g., with a fixed introduced volume of supercritical fluid.

In another aspect, a method of removing and reusing a solvent in a processing solvent stream exiting a processing reactor, the exiting processing solvent stream comprising an azeotropic forming solvent mixture comprising a first solvent and a second solvent is described. In certain embodiments, the method comprises receiving the azeotropic forming solvent mixture in a chamber, exposing the azeotropic forming solvent mixture in the chamber to a supercritical fluid stream at an effective temperature and pressure to remove at least a selected amount, e.g., at least about 25%, at least about 50%, or at least 75% by weight, by weight or by volume of the first solvent, based on the total weight of the azeotropic forming solvent mixture or based on the total volume of the azeotropic forming solvent mixture respectively, from the azeotropic forming solvent mixture, collecting the removed first solvent in the supercritical fluid stream, and providing the collected, removed first solvent to the processing reactor. In some embodiments, at least about 80%, 85%, 90%, 95%, 97%, 98% or 99% by weight or by volume of the first solvent is removed from the solvent mixture. In certain embodiments, the amount removed may be removed with a single charge of the supercritical fluid stream, e.g., with a fixed introduced volume of supercritical fluid.

In another aspect, a method of removing at least a selected amount, e.g., at least about 25%, at least about 50%, or at least 75% by weight, by weight or by volume of NMP, based on the total weight of a solvent mixture or based on the total volume of the solvent mixture respectively, from the solvent mixture comprising NMP and ethylene glycol in a chamber is described. In certain embodiments, the method comprises exposing the solvent mixture comprising the NMP and the ethylene glycol to a supercritical fluid stream of carbon dioxide at an effective temperature and pressure to remove the selected amount, e.g., at least about 25%, at least about 50%, or at least 75% by weight, by weight or by volume of the NMP, based on the total weight of the solvent mixture or based on the total volume of the solvent mixture respectively, from the solvent mixture comprising the NMP and ethylene glycol, and collecting the removed NMP in the supercritical fluid stream of carbon dioxide exiting the chamber. In some embodiments, at least about 80%, 85%, 90%, 95%, 97%, 98% or 99% by weight or by volume of the NMP is removed from the solvent mixture. In certain embodiments, the amount of NMP removed may be removed with a single charge of the supercritical fluid stream, e.g., with a fixed introduced volume of supercritical fluid.

In another aspect, a method comprising removing at least a selected amount, e.g., at least about 25%, at least about 50%, or at least 75%, by weight or by volume of one solvent, based on the weight of a solvent mixture or the total volume of the solvent mixture respectively, the method comprising separating at least the selected amount, e.g., at least about 25%, at least about 50%, or at least 75%, by weight or by volume of the one solvent and an additional solvent into individual components using at least 10% less energy than the energy required to perform the same level of separation using distillation is provided. In some embodiments, at least 20% less energy, at least 30% less energy, at least 40% less energy or at least 50% less energy than the energy required to perform the same level of separation using distillation can be used.

In other embodiments, a method comprising removing at least a selected amount, e.g., at least about 25%, at least about 50%, or at least 75%, by weight or by volume, based on the weight of a solvent mixture or the volume of the solvent mixture respectively, of one solvent in a solvent mixture comprising the one solvent and an additional solvent the method comprising removing at least the selected amount, e.g., at least about 25%, at least about 50%, or at least 75%, of the one solvent and an additional solvent using a total energy input that is at least 10% less than energy than the energy required to perform the same level of removal using distillation is disclosed. In some embodiments, at least 20% less energy, at least 30% less energy, at least 40% less energy or at least 50% less energy than the energy required to perform the same level of separation using distillation can be used.

In an additional aspect, a method comprising removing at least 15% by weight or by volume of one solvent, based on the weight of a solvent mixture comprising the one solvent and an additional solvent or the volume of the solvent mixture, from the solvent mixture comprising the one solvent and the additional solvent in less than 30 seconds from the time in which a supercritical fluid flow in a separation system is switched on. In certain embodiments, at least 15% by weight or by volume of the one solvent can be removed in less than 25 seconds from the time in which a supercritical fluid flow in a separation system is switched on. In other embodiments, at least 15% by weight or by volume of the one solvent can be removed in less than 20 seconds from the time in which a supercritical fluid flow in a separation system is switched on.

Additional features, aspects and examples are described in more detail below.

BRIEF DESCRIPTION OF THE FIGURES

Certain illustrative embodiments are described in more detail below with reference to the accompanying figures in which.

Figure 1:
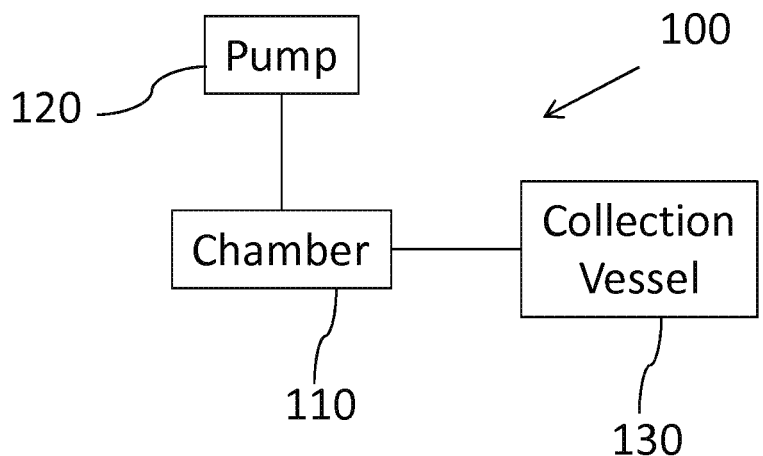
FIG. 1 is an illustration of an open system, in accordance with certain examples.

It will be recognized by the person of ordinary skill in the art, given the benefit of this disclosure, that the relative positions and sizes of the components in the figures are not limiting and that no particular size, dimension, thickness or arrangement is implied as being required based on the representations of the components shown in the figures. Where a particular configuration is shown, the configuration is provided for illustrative purposes only and is not intended to imply that the system require that particular representation for proper function or usage.

DETAILED DESCRIPTION

In certain embodiments described herein a flow or stream of supercritical fluid can be used to remove one solvent from a solvent mixture. While the flow of fluid is shown in certain instances as being from top to bottom, this direction is provided merely for illustrative purposes. If desired, the flow can be configured to be top to bottom, bottom to top, sideways or the like. The flow may be against gravity or may flow in the same general direction as gravity.

In the illustrative embodiments described below, certain configurations of systems and methods effective to extract or remove about 95% or more of one solvent from a solvent mixture, e.g., using a single separation step or using a single charge of supercritical fluid are described. The terms "single separation step" and "single charge of supercritical fluid" are discussed in more detail below. While about 95% or more of one solvent can be removed, it may be desirable to process the removed solvent further using one or more other techniques, e.g., washing, polishing, distillation, drying or other steps commonly used to purify solvents and/or dry them. In other instances, the removed solvent may be pure enough such that no additional processing steps are performed. Similarly, the solvent that remains in the separation vessel or chamber may be subjected to its own processing steps, e.g., washing, polishing, distillation, drying, etc., or may be removed from the chamber and reused without further processing steps.

In certain embodiments, the systems described herein can be effective to separate two or more solvents in a solvent mixture by exposing the solvent to a stream of a supercritical fluid. In some embodiments, the solvent mixture can include two or more solvents that form an azeotrope with each other. Without wishing to be bound by any particular scientific theory, an azeotrope is a mixture of fluids that when distilled provides a vapor phase having about the same ratio of components as the liquid phase. Simple distillation is generally not effective to separate azeotropic solvent mixtures. Azeotropes can generally be categorized as positive and negative azeotropes. For a positive azeotrope, the boiling point temperature of the azeotrope is less than the boiling point temperatures of any of its constituents. For a negative azeotrope, the boiling point temperature of the azeotrope is greater than the boiling point temperatures of any of its constituents. Depending on the exact compositions of the solvent mixtures, they may form positive or negative azeotropes. The systems described herein can be used to separate solvent mixtures that have a tendency to form positive azeotropes or solvent mixtures that have a tendency to form negative azeotropes. Such solvent mixtures are referred to in certain instances herein as azeotropic solvent mixtures.

In certain embodiments, the solvent mixtures described herein can include two or more solvents. In some embodiments, the solvent mixtures may only include two solvents in substantive amounts with other impurities. In other embodiments, the solvent mixtures may include three, four, five or more different solvents. If desired, the solvent mixtures can be subjected to drying steps to remove any water or moisture from them prior to separation but such steps generally are not necessary. The solvent mixtures can be stored at suitable temperatures and pressures prior to separation to avoid any loss due to evaporation. Where solvent mixtures are separated, the separation may occur by exposing a quantity of the solvent mixtures to a supercritical fluid stream, or the same volume of solvent mixture may be divided into multiple separate aliquots each of which is exposed to a supercritical fluid stream to extract one of the solvents from the solvent mixture.

In certain embodiments, a system suitable for separating an azeotropic solvent mixture is shown in FIG. 1. The system 100 includes a chamber 110 configured to receive a solvent mixture. The chamber 110 is fluidically coupled to a pump 120 and a collection vessel 130. In operation of the system 100, the solvent mixture can be introduced into the chamber 110 where the pump 120 has provided a supercritical fluid stream at an effective pressure and temperature to separate one solvent from the solvent mixture. Upon entry of the solvent mixture 110 into the chamber, the conditions in the chamber can be selected such that one of the solvents becomes entrained in the supercritical fluid stream, and the other solvent generally remains out of the stream or insoluble in the stream and can be collected at a desired site, e.g., by draining the second solvent from the chamber 110. The solvent which becomes entrained in the supercritical fluid stream can enter into the collection vessel 130, which can be operated at suitable conditions to condense the solvent that is entrained in the supercritical fluid stream. The solvent can then be drained from the collection vessel 130.

Figure 2:
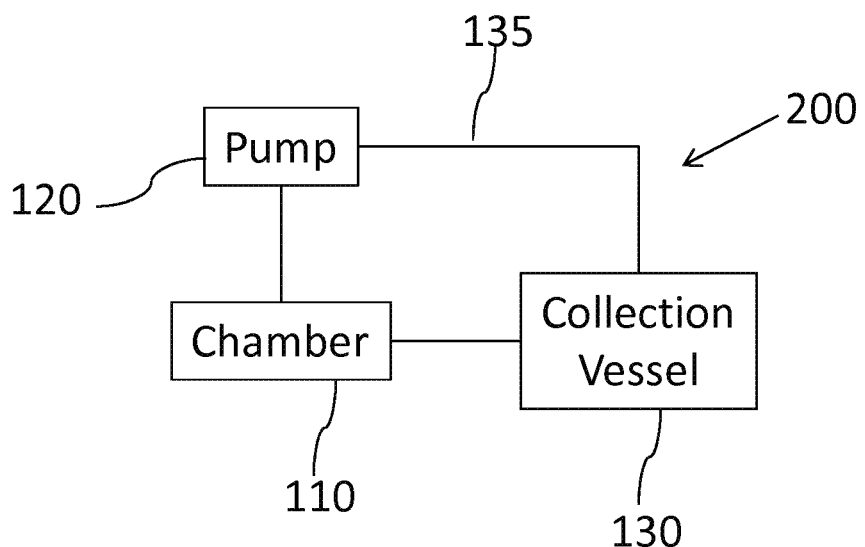
FIG. 2 is an illustration of a closed system, in accordance with certain examples.

In certain examples, the systems described herein can be a closed system or can be an open system, e.g., open to the atmosphere, at some point of the system. While not true in all instances, a closed system is generally expected to provide increased recovery, e.g., 95% or more of one of the solvent can be recovered in an open system and 99% or more would be expected in a typical open system. The depiction in FIG. 1 is an open system. FIG. 2 shows a closed system 200 that includes a recycling line 135 fluidically coupled to the collection vessel 130 and the pump 120. Inclusion of the recycling line permits reuse of the supercritical fluid and provides a more environmentally friendly system. In addition, it may be easier to control the supercritical conditions used in the system when the system is a closed system. In some embodiments, the system 200 can be configured to operate with a fixed amount of supercritical fluid without the need to replenish the source that provides the supercritical fluid. For example, a fixed amount of carbon dioxide can be used in the closed system 200 and the conditions can be selected to provide a supercritical fluid stream of carbon dioxide in the chamber 110. Upon exit of the supercritical fluid stream into the collection vessel, the conditions may be altered such that any solvent entrained in the supercritical fluid stream condenses in the collection vessel 130. Condensed solvent can be drained and optionally subjected to one or more washing steps or polishing steps, e.g., distillation, drying, molecular sieves or the like to further enhance its purity or remove residual amounts of water if present. If desired, one or more traps may be present between the collection vessel 130 and the pump 120, e.g., in the recycling line, to prevent any solvent that remains in the carbon dioxide from reaching the pump 120. In other instances, solvent can be left in the carbon dioxide and passed through the chamber 1120 and the collection vessel 130 to enhance overall recovery yield of the solvent.

In certain embodiments, the chamber 110 can be configured in many different ways. In some embodiments, the chamber is configured to receive a spray of the solvent mixture, e.g., from a nebulizer, aerosolization device or the like, whereas in other instances a volume of solvent can be introduced into the chamber and optionally vaporized prior to exposure to the supercritical fluid stream. Where a spray into the chamber is used, the volume and spray pattern can be selected based on the physical properties of the solvent and the flow rate of the supercritical fluid. In some examples, the flow rate of the supercritical fluid is selected to be the highest possible that still provides separation of the two solvent in the solvent mixture. For example, where NMP and ethylene glycol are separated, the flow rate of the supercritical fluid can be selected to be about 5 L/min to about 25 L/min, more particularly about 10 L/min to about 20 L/min, e.g., about 15-20 L/min. It will be recognized by the person of ordinary skill in the art, given the benefit of this disclosure, that the flow rate may be altered, e.g., higher or lower, depending on the pressure and temperature conditions in the chamber. In addition, the exact flow rate may be less critical than the ratio of supercritical fluid to solvent. In some embodiments, the supercritical fluid:solvent ratio may be about 1:1 to about 30:1, more particularly about 1:1 to about 25:1, for example about 1:1 to about 20:1. In other embodiments, the supercritical fluid:solvent ratio may be about 1:30 to about 1:1, for example about 1:25 to about 1:1, e.g., about 1:20 to about 1:1. The particular supercritical fluid:solvent ratio depends on numerous variables including solubility of the solvent in the supercritical fluid, pressure, temperature and the like.

In some embodiments, the pressure and temperature conditions of the chamber are selected so that one of the solvents in the solvent mixtures becomes entrained in the supercritical fluid stream, and the other solvent generally remains insoluble, but may be miscible, in the supercritical fluid stream under those pressure and temperature conditions. When such conditions are implemented, the phase separation of the two components of the solvent mixture in the supercritical fluid stream permits separation of them in a rapid and cost effective manner using the systems described herein.

Figure 3:
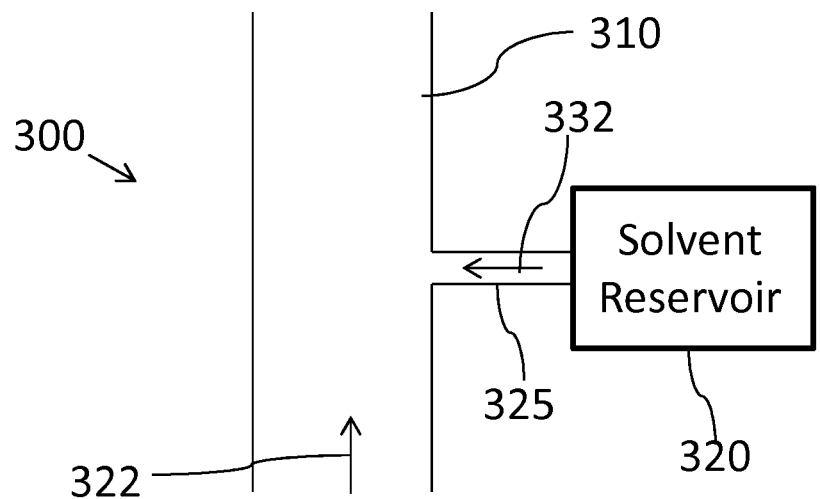
FIG. 3 is an illustration of a chamber, in accordance with certain examples.

In certain embodiments, one illustration of a chamber is shown in FIG. 3. The chamber 300 includes a cavity 310 fluidically coupled at one site to a reservoir 320, which is configured to retain a solvent mixture, through a fluid line 325. The fluid line 325 provides fluid from the solvent reservoir 320 to the cavity 310 generally in the direction shown by arrow 332. The supercritical fluid stream is configured to flow from the bottom of the cavity 310 to the top generally in the direction of arrow 322. The pressure and temperature conditions are selected such that one of the solvents in the solvent mixture becomes entrained in the supercritical fluid stream and the other component or components in the solvent mixture collects at the bottom of the cavity 310 where it can drained. As discussed herein, the solvent can be sprayed into the cavity 310 using a sprayer, nebulizer or similar devices. In the system 300, the fluid line 325 is placed about midway along the longitudinal direction of the cavity 310. Solvent mixture enters the cavity 310, and the solvent that becomes entrained in the supercritical fluid exits the top of the cavity 310 where it can be provided to a collection vessel (not shown). Solvent that phase separates from the supercritical fluid stream can be collected at the base of the cavity 310 and drained from the cavity 310.

Figure 4:
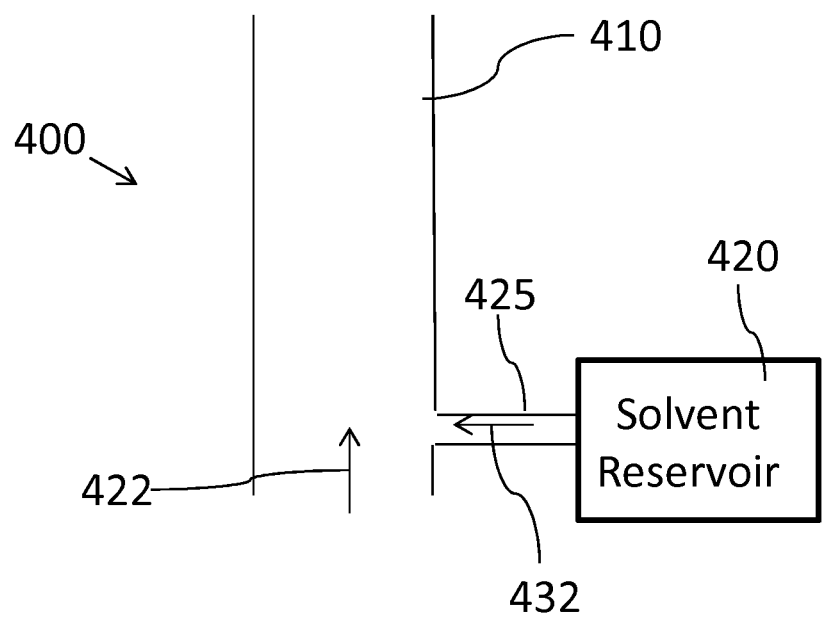
FIG. 4 is another illustration of a chamber, in accordance with certain examples.

In certain examples, another illustration of a chamber is shown in FIG. 4. The chamber 400 includes a cavity 410 fluidically coupled at one site to a reservoir 420, which is configured to retain a solvent mixture, through a fluid line 425. The fluid line 425 provides fluid from the solvent reservoir 420 to the cavity 410 generally in the direction shown by arrow 432. The supercritical fluid stream is configured to flow from the bottom of the cavity 410 to the top generally in the direction of arrow 422. The pressure and temperature conditions are selected such that one of the solvents in the solvent mixture becomes entrained in the supercritical fluid stream and the other component or components in the solvent mixture collects at the bottom of the cavity 410 where it can be drained. As discussed herein, the solvent can be sprayed into the cavity 410 using a sprayer, nebulizer or similar devices. In the system 400, the fluid line 425 is placed toward the bottom of the cavity 410 along the longitudinal direction of the cavity 410. While not wishing to be bound by any particular scientific theory, for certain solvent systems, it may be desirable to provide increased length between where the solvent enters the cavity 410 and exits the cavity 410. In the system 400, solvent mixture enters the cavity 410, and the solvent that becomes entrained in the supercritical fluid exits the top of the cavity 410 where it can be provided to a collection vessel (not shown). Solvent that phase separates from the supercritical fluid stream can be collected at the base of the cavity 410 and drained from the cavity 410.

Figure 5:
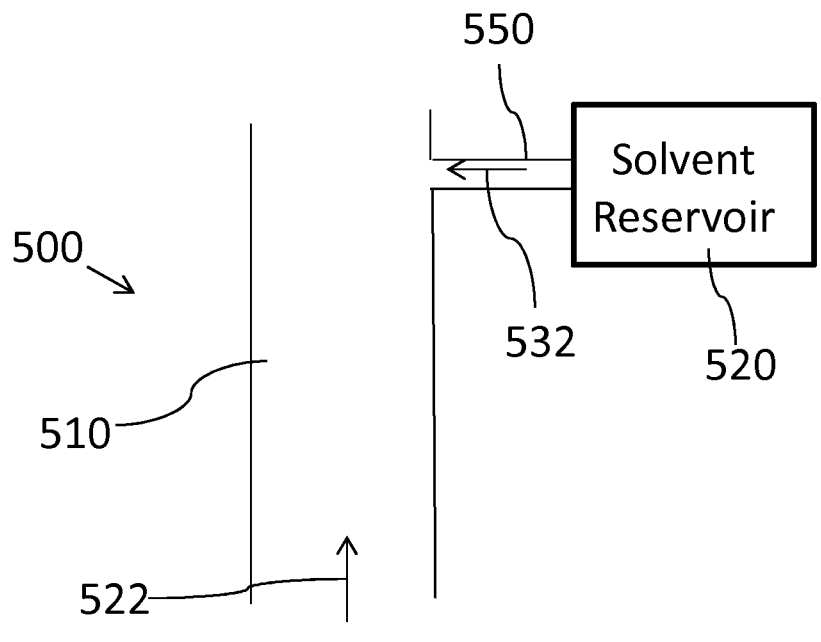
FIG. 5 is an additional illustration of a chamber, in accordance with certain examples.

In some examples, another illustration of a chamber is shown in FIG. 5. The chamber 500 includes a cavity 510 fluidically coupled at one site to a reservoir 520, which is configured to retain a solvent mixture, through a fluid line 525. The fluid line 525 provides fluid from the solvent reservoir 520 to the cavity 510 generally in the direction shown by arrow 532. The supercritical fluid stream is configured to flow from the bottom of the cavity 510 to the top generally in the direction of arrow 522. The pressure and temperature conditions are selected such that one of the solvents in the solvent mixture becomes entrained in the supercritical fluid stream and the other component or components in the solvent mixture collects at the bottom of the cavity 510 where it can be drained. As discussed herein, the solvent can be sprayed into the cavity 510 using a sprayer, nebulizer or similar devices. In the system 500, the fluid line 525 is placed toward the top of the cavity 510 along the longitudinal direction of the cavity 510. While not wishing to be bound by any particular scientific theory, for certain solvent systems, one of the solvent may rapidly phase separate into the supercritical fluid stream and little cavity length 510 may be needed to separate the two solvents. By placing the fluid line 525 near the top of the cavity 510, the solvent that becomes entrained in the supercritical fluid stream can be rapidly separated and isolated without passing the solvent through unneeded flow path in the cavity 510. Solvent that phase separates from the supercritical fluid stream can be collected at the base of the cavity 510 and drained from the cavity 510.

Figure 6:
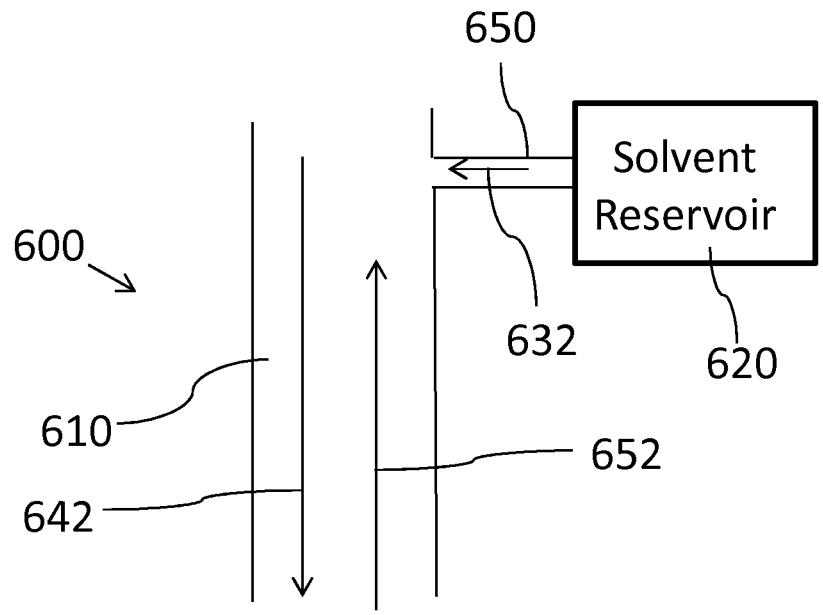
FIG. 6 is another illustration of a chamber, in accordance with certain examples.

In some examples, another illustration of a chamber is shown in FIG. 6. The chamber 600 includes a cavity 610 fluidically coupled at one site to a reservoir 620, which is configured to retain a solvent mixture, through a fluid line 625. The fluid line 625 provides fluid from the solvent reservoir 620 to the cavity 610 generally in the direction shown by arrow 632. The supercritical fluid stream is configured to flow from the bottom of the cavity 610 to the top generally in the direction of arrow 622. The pressure and temperature conditions are selected such that one of the solvents in the solvent mixture becomes entrained in the supercritical fluid stream and the other component or components in the solvent mixture collects at the bottom of the cavity 510 where it can be drained. As discussed herein, the solvent can be sprayed into the cavity 610 using a sprayer, nebulizer or similar devices. In the system 600, the fluid line 625 is placed toward the top of the cavity 610 along the longitudinal direction of the cavity 610. While not wishing to be bound by any particular scientific theory, for certain solvent systems, it may be desirable to first use a counterflow of a supercritical fluid as shown at arrow 642. The counterflow 642 can be introduced by actuating closed a valve that provides the normal flow 652. The counterflow 642 can be used to entrain the solvent mixture as it enters the cavity 610. After some period, the counterflow 642 can be switched off and the normal flow 652 may be resumed by actuating a valve open to provide the normal flow 652. In this manner, increased residence time of the solvent mixture in the cavity 610 can be achieved without increasing the overall length of the cavity 610. Where a counterflow 642 is used, the fluid line 650 can be placed toward the top of the cavity 610 as shown in FIG. 6, or, in other examples, the fluid line 650 could be placed midway along the length of the cavity 610 or toward the bottom of the cavity 610. The solvent that becomes entrained in the supercritical fluid can be isolated as the normal supercritical fluid flow 652 exits the cavity 610 and is provided to a collection vessel (not shown). Solvent that phase separates from the supercritical fluid stream can be collected at the base of the cavity 610 and drained from the cavity 610. In some examples, the counterflow 642 may be the same supercritical fluid as the normal flow 652, whereas in other embodiments, the supercritical fluids may be different. In some examples, the counterflow 642 may not be a supercritical fluid, e.g., can be a gas, and the normal flow 652 can be selected to be a supercritical fluid.

Figure 8:
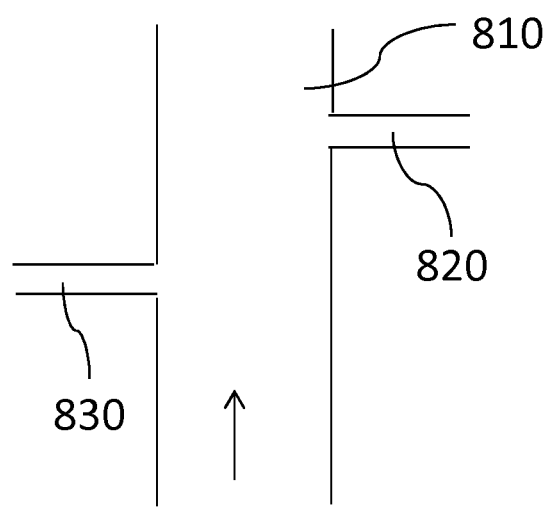
FIG. 8 is another illustration of a chamber comprising multiple entry ports, in accordance with certain examples.
Figure 9:
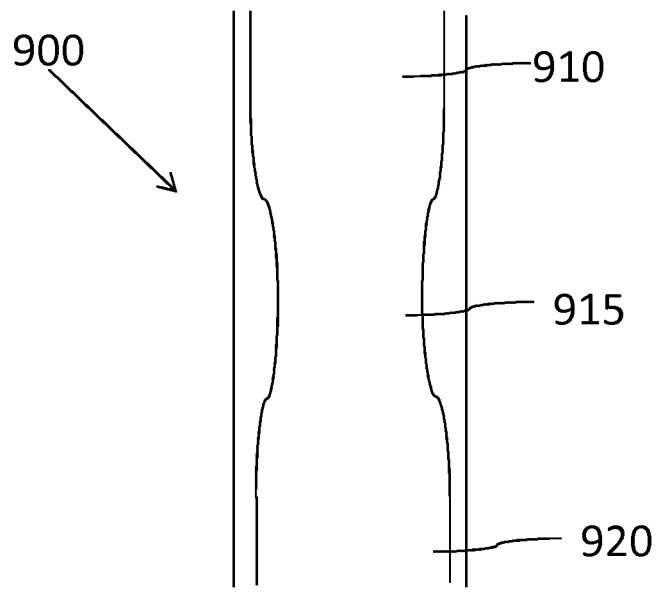
FIG. 9 is an illustration of a chamber with variable inner diameter, in accordance with certain examples.

While the embodiments shown in FIGS. 3-6 use a single chamber and a single point of entry of the solvent into the chamber, many different configurations may also be used. Some illustrative configurations are shown in FIGS. 7-9.

Figure 7:
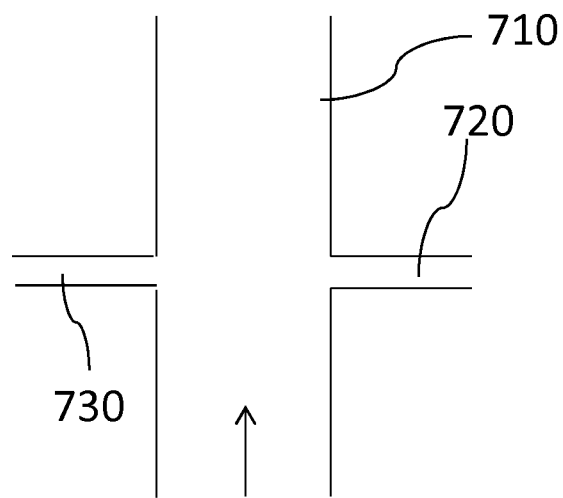
FIG. 7 is an illustration of a chamber comprising multiple entry ports, in accordance with certain examples.

In certain embodiments and referring to FIG. 7, a chamber 700 comprises a cavity 710 and a first port 720 configured to receive a solvent mixture and a second port 730 configured to receive a solvent mixture. In some embodiments, the solvent mixture can be provided to both ports 720, 730 simultaneously or only one of ports 720, 730 can be used at any one time. In some examples, solvent mixture can alternately be pulsed through the ports 720, 730. As discussed herein, a supercritical fluid flow can be provided through the cavity 710 to separate the solvent components in the solvent mixture. In some embodiments, different solvent mixtures can be introduced through the ports 720, 730. For example, a mixture of NMP and water can be introduced through port 720 and a mixture of NMP and ethylene glycol can be introduced through port 730. The conditions can be selected such that NMP becomes entrained in the supercritical fluid stream, whereas the water and the ethylene glycol do not. NMP would exit the cavity 710 in the supercritical fluid stream where it can be collected in a collection vessel (not shown). The water and the ethylene glycol can be collected at the bottom of the cavity 710. Additional ports can also be included in the chamber 700 if desired.

In certain embodiments where a chamber includes two ports, the ports can be offset from each other to introduce solvent mixture into the chamber at different areas of the chamber. One illustration is shown in FIG. 8. The chamber 800 includes a cavity 810 and a first port 820 and a second port 830 offset from the first port 820. In some examples, the solvent mixture can be provided to both ports 820, 830 simultaneously or only one of ports 820, 830 can be used at any one time. In some examples, solvent mixture can alternately be pulsed through the ports 820, 830. As discussed herein, a supercritical fluid flow can be provided through the cavity 810 to separate the solvent components in the solvent mixture. In some embodiments, different solvent mixtures can be introduced through the ports 820, 830. For example, a mixture of NMP and water can be introduced through port 830 and a mixture of NMP and ethylene glycol can be introduced through port 820. The conditions can be selected such that NMP becomes entrained in the supercritical fluid stream, whereas the water and the ethylene glycol do not. NMP would exit the cavity 810 in the supercritical fluid stream where it can be collected in a collection vessel (not shown). The water and the ethylene glycol can be collected at the bottom of the cavity 810. Additional ports can also be included in the chamber 800 if desired.

In certain embodiments, the chambers described herein need not be uniform. In some embodiments, one or more restrictions may be present along the length of the chamber. One illustration is shown in FIG. 9. The chamber 900 comprises a first portion 910 that is coupled to a second portion 920 through a restriction 915. The restriction 915 has a smaller inner diameter than the diameter of portions 910 and 920. While portions 910, 920 are shown as generally having the same diameter, in some instances, the diameter of portion 910 may be different from the diameter of portion 920. In some embodiments, the outer diameter of restriction 915 may also be smaller than the outer diameter of portions 910, 920. In certain embodiments, the restriction 915 may have an inner diameter that is at least 90% less than the inner diameter of the portion 910, more particularly, the inner diameter of portion 915 may be at least 75% less than the diameter of portion 910, e.g., the diameter of portion 915 may be at least 50% less than the diameter of portion 910. While not wishing to be bound by any particular scientific theory, the restriction 915 may be effective to increase the pressure of the chamber 900 by acting to restrict flow of the supercritical fluid through the chamber 900. While the chamber 900 includes three portions, it may be desirable to configure the chamber with only two portions of different size. Depending on the solvents to be separated and the separation conditions, the solvent may be introduced at the portion of the chamber with the smaller diameter or at the portion with the larger diameter.

In certain examples, the chambers used in the systems and methods described herein can be sized and arranged suitably to provide an effective length that permits separation of the components in the solvent mixture. In some embodiments, the column may be about six to about eighteen feet long, more particularly about nine to about fifteen feet long, for example about ten to about 12 feet long. It will be recognized by the person of ordinary skill in the art, given the benefit of this disclosure, that the chamber length may be altered to provide a desired separation within a desired period, e.g., for small volumes of a few liters it may be desirable to size the column about 1 foot long to about 6 feet long. In some examples, the width of the column may be about one inch wide to about twelve inches wide, more particularly, about two inches wide to about ten inches wide, e.g., about three inches wide to about nine inches wide or about five inches wide to about seven inches wide such as, for example about six inches wide. Such large columns may be particularly desired for use in industrial scale separation of the solvent mixtures described herein, though smaller sized columns may be used for separation of small volumes of solvent mixtures, e.g., a few liters or less.

In certain examples, the chambers described herein can include suitable valving and interfaces to provide fluid tight coupling between the solvent reservoirs, supercritical fluid sources, the pumps and the collections vessels. Illustrative valves include a solenoid valve, a 3-way solenoid valve and other valves that can be actuated between open and closed positions. The chamber can include threads configured to receive or mate to threads on fittings, tubing or the like to provide the fluidic coupling between the various components of the system.

In certain embodiments, it may be desirable to use many different chambers in series or in parallel to separate the solvents in the solvent mixture. Where chambers are operated in series, they are generally run side by side or in some arrangement, e.g., carousel or the like. Where chambers are operated in parallel, they generally are coupled to each other such that an exit port of one chamber is coupled to an entry port of another chamber. Numerous different configurations where chambers are operated in parallel are described below. Similar configurations can be used for series operation of multiple chambers.

Figure 10:
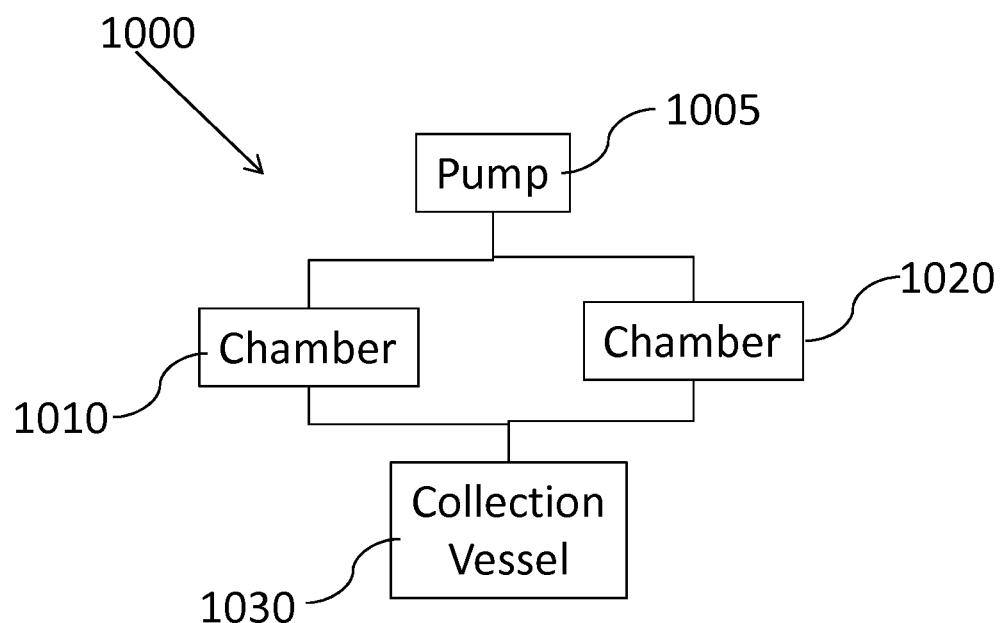
FIG. 10 is an illustration of a system including two chambers, a single pump and a single collection vessel, in accordance with certain examples.

In certain examples and referring to FIG. 10, a system 1000 comprises a first chamber 1010 and a second chamber 1020. Each of the chambers 1010, 1020 is fluidically coupled to a pump 1005 that provides a fluid to the chambers 1010, 1020 and a common collection vessel 1030 that is configured to receive solvent in a supercritical fluid stream from the chambers 1010, 1020. The pump 1005 can be fluidically coupled to each of the chambers 1010, 1020 through a manifold which can include valving that permits each of chambers 1010, 1020 to be used individually or together. Similarly, each of the chambers 1010, 1020 can be fluidically coupled to the collection vessel 1030 through a manifold such that fluid flow from one or both of the chambers can be provided to the collection vessel 1030. While not shown, a recycle line can be present and positioned between the collection vessel 1030 and the pump 1005 or the chambers 1010, 1020 such that supercritical fluid can be provided back to the system 1000. In operation, one solvent from the solvent mixture can be collected in the collection vessel 1030 and the solvent that remains in the chambers 1010, 1020 can be drained at desired intervals.

Figure 11:
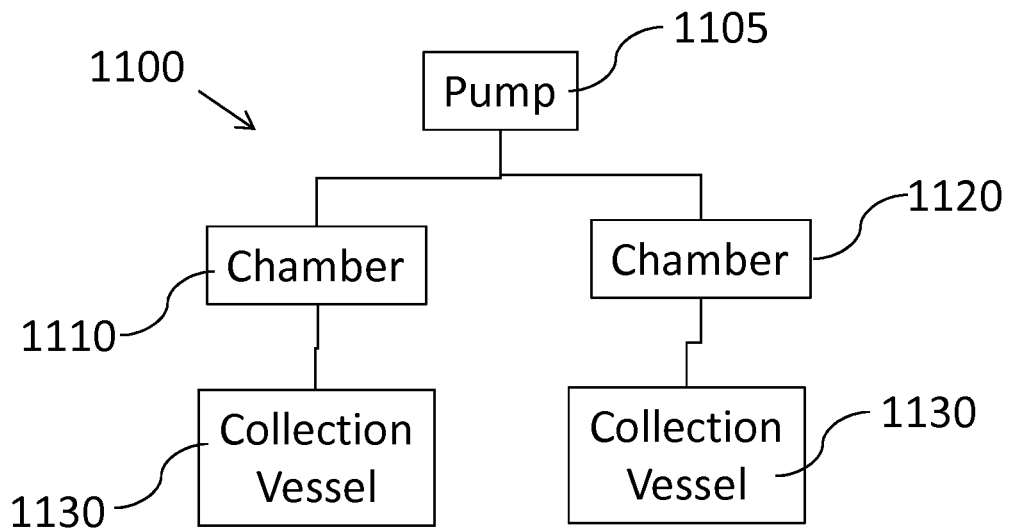
FIG. 11 is an illustration of a system including two chambers, a single pump and two single collection vessels, in accordance with certain examples.

In certain examples and referring to FIG. 11 a system 1100 comprises a first chamber 1110 and a second chamber 1120. Each of the chambers 1110, 1120 is fluidically coupled to a pump 1105 that provides a fluid to the chambers 1110, 1120. Each of the chambers 1110 and 1120 is fluidically coupled to its own collection vessel 1130, 1140, respectively, that are each configured to receive solvent in a supercritical fluid stream from the chambers 1110, 1120. The pump 1105 can be fluidically coupled to each of the chambers 1110, 1120 through a manifold which can include valving that permits each of chambers 1110, 1120 to be used individually or together. For example, it may be desirable to operate a single chamber at any given time and flow can be switched from one chamber to another as desired, e.g., for cleaning of one chamber when the other is being used. While not shown, a recycle line can be present and positioned between each collection vessel 1130, 1140 and the pump 1105 and/or the chambers 1110, 1120 such that supercritical fluid can be provided back to the system 1100.

Figure 12:
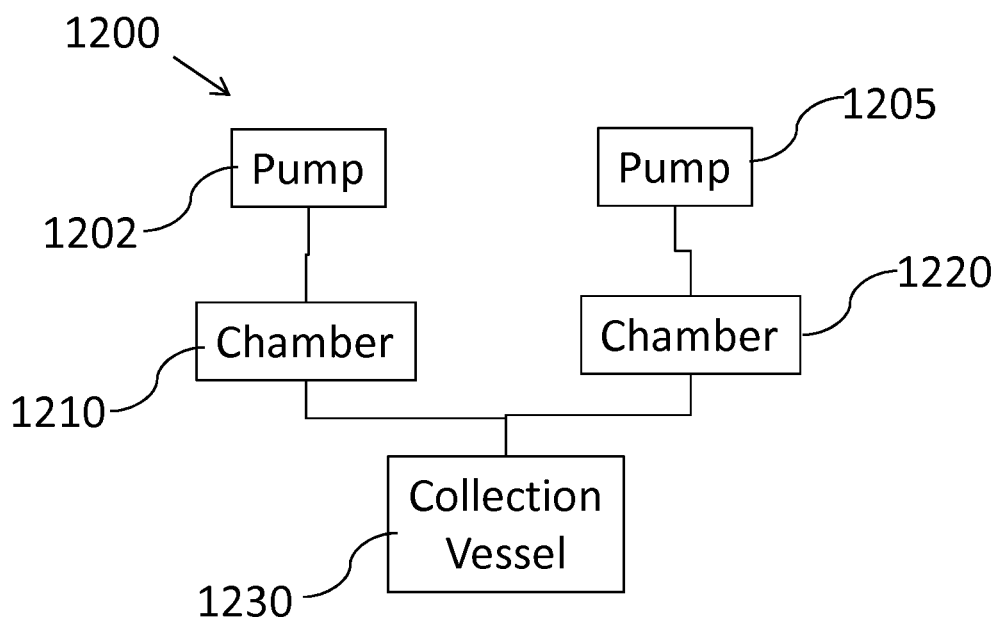
FIG. 12 is an illustration of a system including two chambers, two pumps and a single collection vessel, in accordance with certain examples.

In certain examples and referring to FIG. 12, a system 1200 comprises a first chamber 1210 and a second chamber 1220. Each of the chambers 1210, 1220 is fluidically coupled to its own pump 1202, 1205, respectively, that provides a fluid to the chambers 1210, 1220 and a common collection vessel 1230 that is configured to receive solvent in a supercritical fluid stream from the chambers 1210, 1220. Each of the chambers 1210, 1220 can be fluidically coupled to the collection vessel 1230 through a manifold such that fluid flow from one or both of the chambers can be provided to the collection vessel 1230. While not shown, a recycle line can be present and positioned between the collection vessel 1230 and the pumps 1202, 1205 (or the chambers 1210, 1220 or both) such that supercritical fluid can be provided back to the system 1200. In operation, one solvent from the solvent mixture can be collected in the collection vessel 1230 and the solvent that remains in the chambers 1210, 1220 can be drained at desired intervals. The inclusion of two pumps 1202, 1205 permits independent operation and flow control to the chambers 1210, 1220. Independent operation of the chambers 1210, 1220 may be desirable where the chambers 1210, 1220 are sized differently or where different solvent mixtures are provided to the different chambers.

Figure 13:
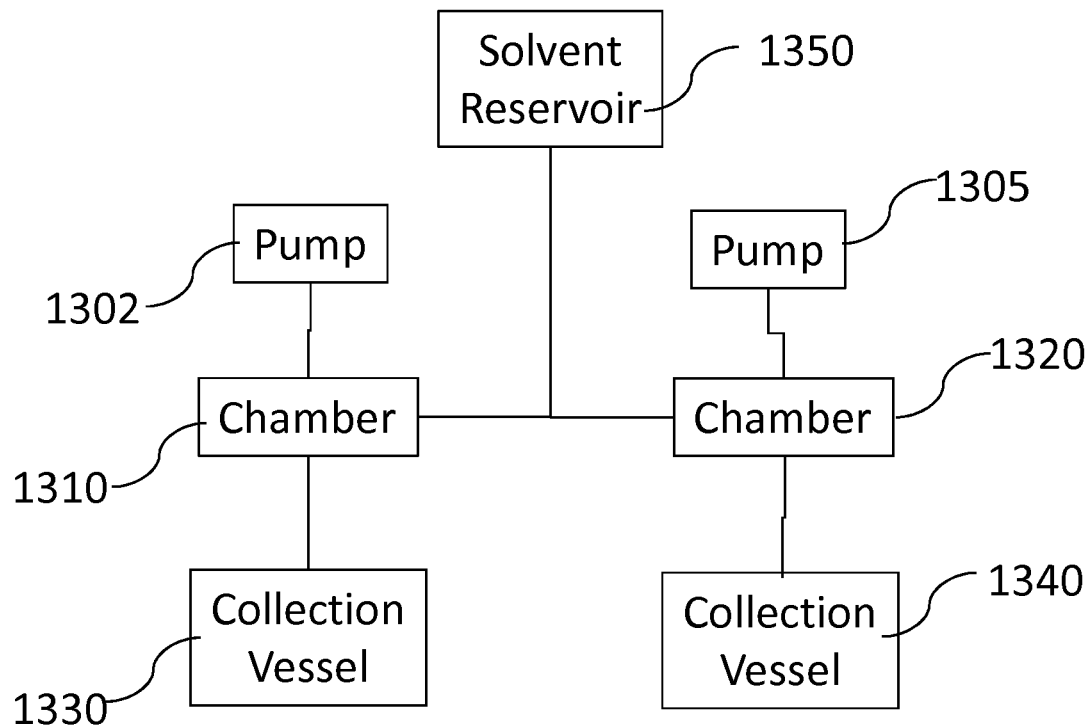
FIG. 13 is an illustration of a system including two chambers, two pumps and two collection vessels, in accordance with certain examples.

In certain embodiments and referring to FIG. 13, a system 1300 comprises a first chamber 1310 and a second chamber 1320. Each of the chambers 1310, 1320 is fluidically coupled to its own pump 1302, 1305, respectively, that provides a fluid to the chambers 1310, 1320. Each of the chambers 1310 and 1320 is fluidically coupled to its own collection vessel 1330, 1340, respectively, that are each configured to receive solvent from a solvent reservoir 1350 and separate the solvents in the mixture using supercritical fluid from the pumps 1302, 1305. While not shown, a recycle line can be present and positioned between the collection vessels 1330, 1340 and the pumps 1302, 1305 (or the chambers 1310, 1320 or both) such that supercritical fluid can be provided back to the system 1300.

Figure 14:
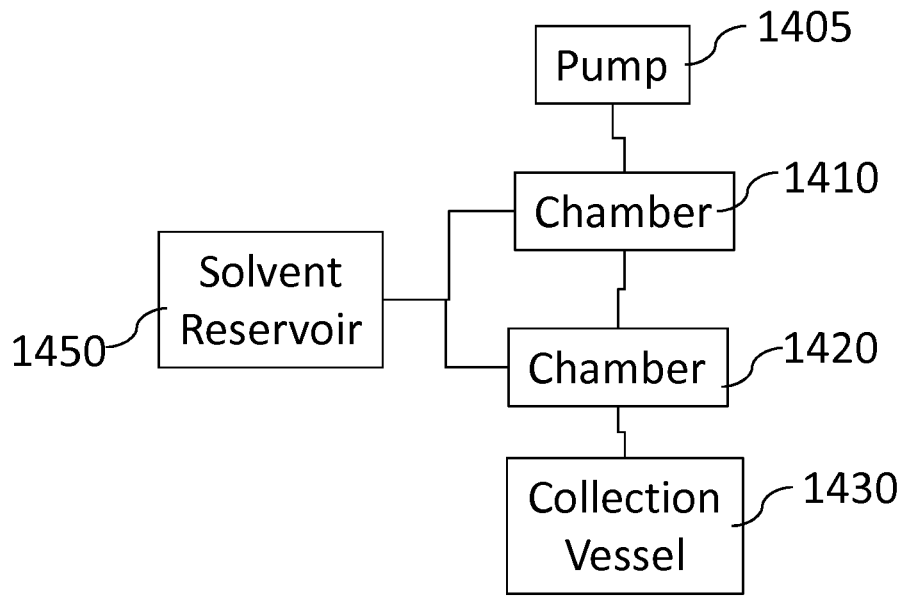
FIG. 14 is an illustration of a system including two chambers configured to operate in series, in accordance with certain examples.

In certain embodiments and referring to FIG. 14, a system 1400 is shown where the chambers are operated in series. The system 1400 includes a first chamber 1410 and a second chamber 1420 fluidically coupled to the first chamber 1410. A pump 1405 is fluidically coupled to the first chamber 1410. A collection vessel 1430 is fluidically coupled to the second chamber 1420. A solvent reservoir 1450 is fluidically coupled to each of the first chamber 1410 and the second chamber 1420. Solvents may independently be provided to the first and second chambers 1410, 1420 from the solvent reservoir 1450. If desired, each of the first and second chambers 1410, 1420 can include independent pressure and/or temperature control such that differential separation may occur in the different chambers. The collection vessel 1430 may receive the supercritical fluid stream from the second chamber 1420 and can include temperature control to condense the solvent in the supercritical fluid stream. While not shown, a recycle line can be present and positioned between the collection vessels 1430 and the pumps 1402 or the first and second chambers 1410, 1420 such that supercritical fluid can be provided back to the system 1400.

In certain embodiments, the systems can include more than two chambers, more than two pumps and more than two collection vessels if desired. In some embodiments, it may be desirable to have three, four, five, six or more separate chambers each of which can receive solvent mixture and a supercritical fluid to speed up the overall removal of one solvent from the solvent mixture. Each chamber may have independent temperature and pressure control or the chambers may all be positioned in a cell or reactor and controlled through common control means.

In certain embodiments, the chambers in the systems described herein may be produced from plastics, metals, non-metals, glasses, refractories and other materials. The materials are desirably inert and solvent-resistant such that they do not flake, etch or otherwise deteriorate when exposed to solvents or solvent mixtures. If desired, the inner portion of the chamber that is exposed to solvent may be coated with an inert material to enhance the solvent resistance even further. The non-reactive nature of the supercritical fluids used herein permits reuse of them in successive separations. In some embodiments, the system can be charged with a fixed amount of fluid that is used over and over again without introduction of new fluid.

In certain examples, the chambers described herein can be linear, circular, or may take other geometric forms to provide an overall desired length. In some embodiments, the chambers can be circular in form such that the overall space occupied by the chamber is less than if it were a linear chamber.

In certain embodiments, the pumps used in the systems described herein can be fluidically coupled to a source of fluid, e.g., a gas, liquid or the like, and used to pressurize the fluid and/or provide temperature control to the fluid to place the fluid in a supercritical state for use in the systems described herein. While the exact supercritical fluid used may vary from solvent mixture to solvent mixture, illustrative supercritical fluids suitable for use include those that are generally inert and non-reactive with the solvent mixtures to be separated. Exemplary supercritical fluids suitable for use include, but are not limited to, carbon dioxide, water, methane or extracted or provided natural gas including any intrinsic impurities, ethane, propane, ethylene, propylene, methanol, ethanol and acetone. Where carbon dioxide is used, its critical temperature and pressure are 304.1 Kelvin and 7.38 MPa, respectively, and its critical density is 0.469 $g/cm^3$. Where water is used as a supercritical fluid, its critical temperature and pressure are 647.096 Kelvin and 22.064 MPa, respectively, and its critical density is 0.322 $g/cm^3$. Where methane is used as a supercritical fluid, its critical temperature and pressure are 190.4 Kelvin and 4.60 MPa, respectively, and its critical density is 0.162 $g/cm^3$. Where ethane is used as a supercritical fluid, its critical temperature and pressure are 305.3 Kelvin and 4.87 MPa, respectively, and its critical density is 0.203 $g/cm^3$. Where propane is used as a supercritical fluid, its critical temperature and pressure are 369.8 Kelvin and 4.25 MPa, respectively, and its critical density is 0.217 $g/cm^3$. Where ethylene is used as a supercritical fluid, its critical temperature and pressure are 282.4 Kelvin and 5.04 MPa, respectively, and its critical density is 0.215 $g/cm^3$. Where propylene is used as a supercritical fluid, its critical temperature and pressure are 364.9 Kelvin and 4.60 MPa, respectively, and its critical density is 0.232 $g/cm^3$. Where methanol is used as a supercritical fluid, its critical temperature and pressure are 512.6 Kelvin and 8.09 MPa, respectively, and its critical density is 0.272 $g/cm^3$. Where ethanol is used as a supercritical fluid, its critical temperature and pressure are 513.9 Kelvin and 6.14 MPa, and its critical density is 0.276 $g/cm^3$. Where acetone is used as a supercritical fluid, its critical temperature and pressure are 508.1 Kelvin and 4.70 MPa, respectively, and its critical density is 0.278 $g/cm^3$. The pump may be used along with temperature and pressure control to pressurize the fluid to the supercritical pressure and heat the fluid to the supercritical temperature to provide the supercritical fluid stream to the chamber. If desired, the chamber may include a heat jacket to maintain the supercritical fluid at the supercritical temperature during the separation of the solvents. The particular fluid selected will depend on the physical properties of the solvent or solvent mixture including, but not limited to, solubility parameters, dielectric strengths, polarity or other suitable physical parameters.

In certain embodiments, the pump can be fluidically coupled to a source of the supercritical fluid, whereas in other embodiments, a generator of the fluid can be used to provide the supercritical fluid source. For example, a $CO_2$ gas cylinder or a $CO_2$ generator can be used to provide carbon dioxide for pressurization and temperature control. In some embodiments, the heating and/or pressurization of the fluid can occur prior to delivery to the chamber, whereas in other examples, the fluid may be pre-heated and/or pre-pressurized, but the supercritical state is not reached until the fluid is provided to the chamber.

In certain embodiments, the exact flow rate used in the separation may vary from solvent mixture to solvent mixture. In some embodiments, the flow rate can be about 1 Liters/minute to about 50 Liters/minute, more particularly about 5 Liters/minute to about 35 Liters/minute, e.g., about 15-20 Liters/minute. In some embodiments, the flow rate of the supercritical fluid is selected to provide a solvent recovery in the collection vessel that is greater than what can be recovered using distillation within the same time period. In some embodiments, the system can be designed to separate the solvents at a feed rate of at least 250 pounds/hour, more particularly at a rate of at least 350 pounds/hour, e.g., 375-425 pounds/hour or more. Where such large rates are achieved, it may be desirable to also use substantial amounts of the supercritical fluid to provide the supercritical fluid flow. For example, it may be desirable to use supercritical fluid in an amount that is at least twenty times greater than the desired pounds of solvent per hour, more particularly at least twenty-five times greater than the pounds of solvent per hour, e.g., where the desired solvent pounds per hour is about 400 pounds per hour, the amount of supercritical fluid used can be about thirty times that value or about 12,000 pounds per hour.

Figure 15:
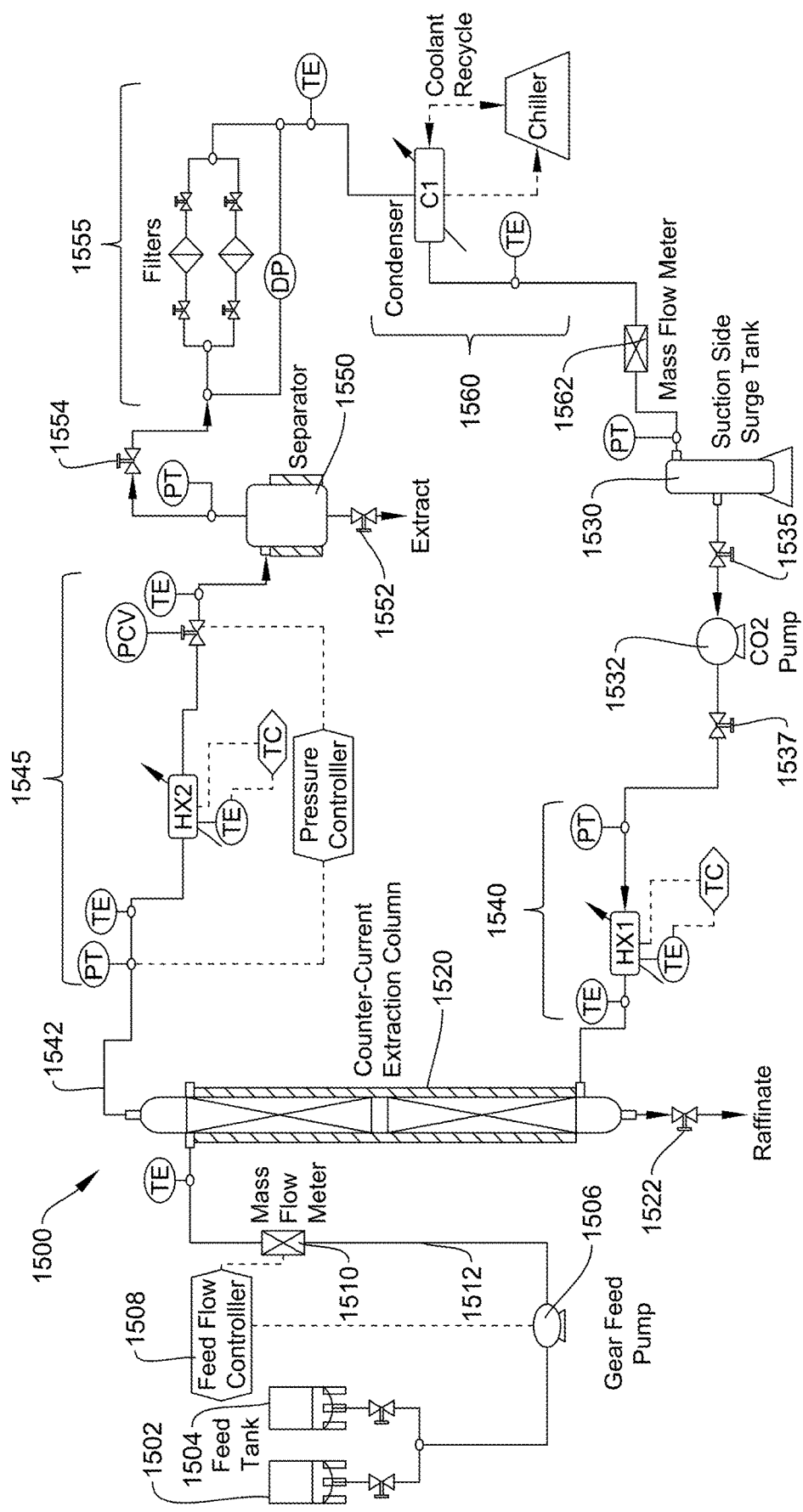
FIG. 15 is an illustration of an industrial scale system configured to separate large quantities of solvent in a solvent mixture, in accordance with certain examples.

In certain embodiments, high volume separations can be performed using an industrial scale system configured to receive solvent mixture from a tanker truck or feed tanks. One such system is shown in FIG. 15. The system 1500 comprises two solvent mixture feed tanks 1502, 1504 fluidically coupled to a pump 1506. The pump can be controlled using feed flow controller 1508 to control the flow rate of fluid to the system. The exact flow rate can be monitored using a mass flow meter 1510. The feed tanks 1502, 1504 are fluidically coupled to a chamber 1520 through a fluid line 1512. As shown in FIG. 15, the solvent mixture is provided to the chamber 1520 at a single point of entry at the top of the chamber 1520, but as discussed herein, other entry points and/or multiple entry points may also be used to introduce the solvent mixture into the chamber 1520. As solvent mixture is introduced into the top of the chamber 1520, a supercritical fluid stream is introduced into the bottom of the chamber 1520. It may be desirable to first introduce solvent mixture into the top of the chamber 1520 and then halt the flow of solvent mixture into the chamber 1520 as the supercritical fluid flow is introduced from the bottom of the chamber 1520. A fluid tank 1530 is fluidically coupled to a pump 1532 through a valve 1535 which can be opened to permit gas to flow from the tank 1530 to the chamber 1520. Temperature and pressure control can be provided by module 1540 to place the fluid from the tank 1530 into a supercritical state and provide the supercritical fluid flow to the chamber 1520. The supercritical conditions, the type of supercritical fluid and the flow rates are selected such that expansion of the solvent mixture in the chamber 1520 in the presence of the supercritical fluid flow removes one of the solvents in the solvent mixture into the supercritical fluid flow and leaves the other solvent of the solvent mixture behind in the chamber 1520. The solvent that remains behind can be drained off as a raffinate through a valve 1522 at the bottom of the chamber 1520. If desired, the valve 1522 may be opened in periodic intervals to remove raffinate from the chamber 1520. Such opening desirably occurs when no solvent mixture is being introduced into the chamber 1520, though the system 1500 can be operated in an open state where raffinate is drained during operation of the system 1500. The solvent that becomes entrained in the supercritical fluid stream exits the column and the top and enters a fluid flow line 1542. The fluid flow line 1542 is fluidically coupled to a collection vessel 1550. A pressure/temperature control module 1545 can be used to provide pressure reduction of the exiting supercritical fluid flow such that the entrained solvent precipitates or condenses out of the supercritical fluid. The extracted solvent can then be removed from the system by opening valve 1552. The fluid used to provide the supercritical fluid flow can be recycled back to the fluid tank 1530 by opening a valve 1554 to permit flow of fluid through a filter module 1555 and a condenser module 1560. Flow of the fluid back to the tank 1530 can be monitored with flow controller 1562. Each of the valves 1522 and 1552 can be fluidically coupled to a pump (not shown) such that the raffinate and extract, respectively, are pumped to storage tanks or a tanker truck. Where the system 1500 is configured for in-line removal of a solvent in a solvent mixture, each of the raffinate and the extract may be pumped back to the reactor for re-use.

In some embodiments, an in-line system can be configured for down hole operation to provide real-time separation of solvent-like materials that may be present during oil/gas exploration operations. For example, a small amount of fluid can be removed down hole and separated using the systems described herein to determine the level of each material in the fluid. In some embodiments, the natural gas, e.g., methane, that is present may be used as a supercritical fluid itself to provide the separation of the solvent-like materials in the fluid stream.

In certain embodiments, the systems described herein can be used in water purification operations or as water purification systems. By selecting effective temperatures and pressures for the supercritical fluid, water can be separated from impurities to provide substantially pure water. In some instances, the water purification system can be sized and arranged to provide municipal drinking water, whereas in other embodiments, the system can be sized and arranged for household use, e.g., can be placed at the water service entrance to the house to provide substantially pure water throughout the house or can be placed under a sink to provide substantially pure water from the sink. The residential systems desirably operate off of 110V AC, though whole house configurations may operate off of 220V AC if desired. The household system can include a supercritical fluid source tank, e.g., a $CO_2$ tank, a chamber for receiving water from the public water feed or from a well, an collection vessel designed to receive the purified water, and a pump configured to provide supercritical fluid to the chamber to effectuate separation of the water from impurities in the water. The chamber can include a drain that is periodically opened to drain the impurities into the sewer system or septic system of the house. Purified water can be stored in the collection vessel until ready for use. If desired, the purified water can be subjected to ozonation, ultraviolet light or other means to remove any microbials that may be present. In addition, other steps such as polishing steps to add back desired minerals to enhance taste may also be performed.

In certain embodiments, the supercritical fluid removes about 95% or more by weight of one of the solvents from the solvent mixture. In some instances, such amounts may be removed with a single charge of supercritical fluid or using a single separation step. Single charge or single separation step refers to a single pass of the supercritical fluid through the chamber and to the collection vessel. To increase the overall amount of solvent recovery, the supercritical fluid exiting the collection vessel may be recycled to the chamber for removal of any residual amounts in the supercritical fluid. For example, in some instances, the systems and methods described herein can be used to provide 96% by weight, 97% by weight, 98% by weight, 99% by weight or more recovery of the solvent from the solvent mixture.

In certain embodiments, the collection vessel can be configured to receive the supercritical fluid stream from the chamber and condense the entrained solvent in the supercritical fluid stream. For example, the collection vessel can include a pressure valve to alter the pressure of the supercritical fluid stream. In some embodiments, the pressure valve is configured to reduce the pressure of the supercritical fluid and permit condensing out of the solvent. The solvent is generally collected in the collection vessel and can be drained off or pumped to a desired container for further processing and/or storage. The collection vessel may include a fluid line back to the chamber or back to the pump or both to receive the separation fluid from the collection vessel for reuse. The recycle line can include one or more valves to permit provision of the fluid at certain time and prevent flow of the fluid back to the pump and/or chamber at other times of operation of the system.

In certain embodiments, the system can include a detector, before, after or in the collection vessel to verify the purity of the solvent in the supercritical fluid stream. In some instances, the detector can be in-line and positioned between the chamber and the collection vessel to ensure that the solvents have been separated prior to permitting any condensation in the collection vessel. Such detectors include, but are not limited to, infrared detectors, visible light detectors, ultraviolet light detectors, fluorescence detectors, magnetic resonance detectors and other detectors commonly used to detect chemical species.

In certain examples, the collection vessel can be fluidically coupled to a dryer to pass the supercritical fluid to the dryer prior to providing it back to the system. Such drying can be configured to remove any water or moisture from the supercritical fluid, in cases where the supercritical fluid is not water, prior to reintroduction of the fluid into the system.

In certain embodiments, the systems described herein can be configured for operation using 110 Volts, 220 Volts, 12 Volts DC or other power sources such as fuel cells, batteries, solar cells or the like. The systems described herein generally require substantially less power and less physical space than conventional distillation systems, which makes the systems described herein more "green" and environmentally friendly than conventional distillation systems.

In certain examples, the systems described herein can be used as an in-line solvent purification system configured to remove about 95% or more of at least one solvent from an azeotropic solvent mixture. By placing the system in-line, the solvent which is removed can be provided back upstream for reuse in the processing operation. The in-line solvent purification system can include a first port configured to couple to a processing solvent stream exiting a reactor. The fluid stream can be provided to a chamber where separation of the solvent components can occur. For example, a pump fluidically coupled to the chamber can provide a supercritical fluid stream at an effective temperature and pressure to the azeotropic solvent mixture in the chamber to remove at least about 95% of a first solvent from the azeotropic solvent mixture. The removed solvent can be provided to a collection vessel fluidically coupled to a second port of the chamber and configured to receive the removed solvent in the supercritical fluid stream exiting the second port of the chamber. A fluid line between the collection vessel and the reactor can provide removed solvent back to the reactor for subsequent use. Similarly, a fluid line between the chamber and the reactor can provide solvent remaining in the chamber back to the reactor for subsequent use. By separating and recycling the solvents in-line, substantially less solvent can be used in a processing operation.

The systems described herein can be used to separate many different types of solvents in a solvent mixture. In certain examples, at least one of the solvents in the solvent mixture is an organic solvent or an inorganic solvent. In some embodiments, the solvents may both be (or all be) organic solvents. In other examples, the solvents may both be (or all be) inorganic solvents. Where organic and inorganic solvents are present in solvent mixture, it may be desirable to permit phase separation of the organic and inorganic solvents and remove them using conventional extraction/separation techniques prior to exposing the different solvents to the supercritical fluid stream.

Numerous illustrative examples of binary solvent systems and ternary solvent systems are discussed below. The term binary system refers to the presence of two solvents and is not intended to exclude impurities or other minor amounts of substances that may be present. The term ternary system refers to the presence of three solvents and is not intended to exclude impurities or other minor amounts of substances that may be present. The illustrative solvent systems described herein are generally named according to IUPAC nomenclature or in certain instances, the common chemical name. For convenience purposes below, the term "binary system" is used in certain instances as combinations of at least two solvents are envisioned. Where the illustrative binary systems referred to below describe a particular solvent in combination with "one of" or "at least one of" an additional solvent, where a single additional solvent is present, the system would be a binary system. Where two additional solvents are present, the system would be a ternary system. Where three additional solvents are present, the system would be a quaternary system. While two or more solvents may be present, additional impurities, trace contaminants and the like may also be present in the solvent system.

In other embodiments, the systems and methods described herein can be used to separate a binary system comprising N-methyl-2-pyrrolidone (NMP) and at least one of a di-ol, e.g., ethylene glycol, water and propylene carbonate.

In other embodiments, the systems and methods described herein can be used to separate a binary system comprising trichlorofluoromethane and at least one of acetaldehyde, methyl formate and 2-methylbutane.

In some examples, the systems and methods described herein can be used to separate a binary system comprising trichloronitromethane and at least one of acetic acid, ethyl alcohol, isopropyl alcohol, propyl alcohol, isoamyl alcohol, n-pentanol, toluene, methylcyclohexane, and n-heptane.

In certain examples, the systems and methods described herein can be used to separate a binary system comprising carbon tetrachloride and at least one of carbon disulfide, chloroform formic acid, nitromethane, methyl alcohol, acetonitrile, acetic acid, ethyl alcohol, acrylonitrile, acetone, propyl alcohol, thiophene, butyl nitrite, butyl alcohol, ethyl ether, pyridine, benzene, n-heptane and o-xylene.

In some embodiments, the systems and methods described herein can be used to separate a binary system comprising carbon disulfide and at least one of chloroform, formic acid, nitromethane, methyl alcohol, acetic acid, propyl nitrite, ethyl alcohol, acetone, propyl alcohol, ethyl acetate, n-pentane, n-hexane or toluene.

In certain embodiments, the systems and methods described herein can be used to separate a binary system comprising bromodichloromethane and at least one of nitromethane, methyl alcohol, ethyl alcohol, ethyl acetate, benzene, cyclohexane, or n-hexane.

In other embodiments, the systems and methods described herein can be used to separate a binary system comprising bromoform and at least one of formic acid, acetamide butyric acid, phenol, aniline, toluene, o-cresol, or alpha-pinene.

In certain examples, the systems and methods described herein can be used to separate a binary system comprising chloroform and at least one of formic acid, methyl alcohol, ethyl alcohol, acetone, propyl alcohol, p-dioxane, cyclohexane, methylcyclopentane, n-hexane or toluene.

In some embodiments, the systems and methods described herein can be used to separate a binary system comprising formic acid and at least one of nitromethane, trichloroethylene, tetrachloroethylene, acetic acid, nitroethane, ethyl ether, ethyl sulfide, pyridine, 2-methylbutane, n-pentane, bromobenzene, chlorobenzene, fluorobenzene, benzene, aniline, 2-picoline, cyclohexane, methylcyclopentane, n-hexane, propyl sulfide, isopropyl sulfide, toluene, -o-chlorotoluene, methylcyclohexane, n-heptane, styrene, o-xylene, m-xylene, or n-octane.

In certain embodiments, the systems and methods described herein can be used to separate a binary system comprising bromomethane and methyl alcohol.

In other embodiments, the systems and methods described herein can be used to separate a binary system comprising iodomethane and at least one of methyl alcohol, ethyl alcohol, acetone, n-hexane, nitromethane, methyl alcohol, acetic acid, ethyl alcohol, propyl alcohol, p-dioxane, n-butyl alcohol, n-pentane, cyclohexane, methylcyclopentane, n-hexane, toluene, n-heptane, styrene, o-xylene, n-octane, cumene, mesitylene, n-nonane, n-decane, n-undecane, or n-dodecane.

In certain examples, the systems and methods described herein can be used to separate a binary system comprising methyl nitrate and at least one of methyl alcohol, cyclohexane, n-hexane, n-heptane In certain examples, the systems and methods described herein can be used to separate a binary system comprising methyl alcohol and at least one of trichloroethylene, bromoethane, acetic acid, acetone, methyl acetate, thiophene, methyl acrylate, p-dioxane, ethyl sulfide, pyridine, cyclopentane, isobutyl formate, piperidine, n-pentane, chlorobenzene, fluorobenzene, benzene, cyclohexane, toluene, methylcyclohexane, n-heptane, o-xylene, n-octane, n-nonane, n-decane or methyl tert-butyl ether.

In some examples, the systems and methods described herein can be used to separate a binary system comprising tetrachloroethylene and at least one of acetic acid, acetamide, ethylene glycol, acetone, propionic acid, propyl alcohol, n-butyl alcohol, pyridine, n-amyl alcohol or toluene.

In certain examples, the systems and methods described herein can be used to separate a binary system comprising hexachloroethane and at least one of trichloroacetic acid, phenol, aniline, benzyl alcohol or p-cresol.

In certain embodiments, the systems and methods described herein can be used to separate a binary system comprising trichloroethylene and at least one of acetic acid, benzene, cyclohexane or n-heptane.

In some embodiments, the systems and methods described herein can be used to separate a binary system comprising trichloroacetic acid and at least one of pentachloroethane, naphthalene or butylbenzene.

In certain embodiments, the systems and methods described herein can be used to separate a binary system comprising bromoacetic acid and at least one of o-dichlorobenzene, o-bromotoluene, acetophenone, butylbenzene or cymene.

In other embodiments, the systems and methods described herein can be used to separate a binary system comprising chloroacetic acid and at least one of bromobenzene, phenol, m-bromotoluene, p-bromotoluene, styrene, o-xylene, m-xylene, n-octane, cumene, mesitylene, pseudocumene, naphthalene, cymene, n-decane or 1,3,5-triethylbenzene.

In some examples, the systems and methods described herein can be used to separate a binary system comprising acetonitrile and at least one of acetic acid, ethyl alcohol, pyridine, isoprene, isopropyl acetate, toluene, ethylbenzene or n-undecane.

In other examples, the systems and methods described herein can be used to separate a binary system comprising acetaldehyde and at least one of acetone, ethyl ether or benzene.

In certain examples, the systems and methods described herein can be used to separate a binary system comprising thioacetic acid and at least one of benzene, cyclohexane, or methylcyclopentane.

In some examples, the systems and methods described herein can be used to separate a binary system comprising acetic acid and at least one of nitroethane, dioxane, acetone, pyridine, 2-picoline, 3-picoline, 4-picoline, benzene, cyclohexane, n-hexane, isopropyl sulfide, toluene, triethylamine, 2,6-lutidine, methylcyclohexane, n-heptane, styrene, ethylbenzene, o-xylene, m-xylene, p-xylene, ethylcyclohexane, n-octane, cumene, mesitylene, n-nonane, n-decane or n-undecane.

In other embodiments, the systems and methods described herein can be used to separate a binary system comprising ethylene sulfide and at least one of acetone, n-hexane or 2,3-dimethylbutane.

In certain examples, the systems and methods described herein can be used to separate a binary system comprising methyl formate and at least one of ethyl ether, isoprene, 2-methylbutane, n-pentane, n-hexane or 2,3-dimethylbutane.

In additional examples, the systems and methods described herein can be used to separate a binary system comprising iodoethane and at least one of ethyl alcohol, propyl alcohol or n-hexane.

In certain examples, the systems and methods described herein can be used to separate a binary system comprising acetamide and at least one of benzaldehyde, methylaniline, m-cresol, styrene, o-xylene, m-xylene, p-xylene, 2,4-xylenol, 3,4-xylenol, ethylaniline, quinolone, indene, naphthalene, safrol, eugenol, p-cymene, diethylaniline, camphene, dipentene, camphor, isoamyl valerate, isoamyl sulfide, 1-methylnaphthalene, 2-methylnaphlhalene, acenaphthene, biphenyl, phenyl ether, diphenylmethane, 1-2-diphenylethane or benzyl ether.

In some examples, the systems and methods described herein can be used to separate a binary system comprising nitroethane and at least one of m-hexane or toluene.

In certain examples, the systems and methods described herein can be used to separate a binary system comprising ethyl nitrate and at least one of thiophene, benzene, cyclohexane, n-hexane or n-heptane.

In other examples, the systems and methods described herein can be used to separate a binary system comprising ethyl alcohol and at least one of acrylonitrile, acetone, ethyl sulfide, pyridine, cyclopentane, n-pentane, fluorobenzene, benzene, cyclohexane, n-hexane, propyl ether, toluene, ethylbenzene, p-xylene or n-octane.

In some embodiments, the systems and methods described herein can be used to separate a binary system comprising ethylene glycol and at least one of pyridine, benzene, phenol, aniline, o-bromotoluene, o-nitrotoluene, toluene, m-toluidine, o-cresol, m-cresol, 2,6-lutidine, n-heptane, styrene, m-xylene, p-xylene, 3,4-xylenol, 2,4,6-collidine, 2,4-xylidine, butyl ether, quinoline, indene, cumene, mesitylene, propylbenzene, cymene, camphene, camphor, menthol, n-decane, naphthalene, 1-methylnaphthalene, 2-methylnaphthalene, acenaphthene, biphenyl, fluorene, diphenylmethane, benzyl phenyl ether, n-tridecane, anthracene or stilbene.

In other embodiments, the systems and methods described herein can be used to separate a binary system comprising methyl sulfide and at least one of acetone, isoprene, cyclopentane, n-pentane or 2,2-dimethytbutane.

In additional embodiments, the systems and methods described herein can be used to separate a binary system comprising methyl disulfide and at least one of n-heptane or 2,3-dimethylhexane.

In other instances, the systems and methods described herein can be used to separate a binary system comprising ethylenediamine and at least one of n-butyl alcohol, benzene or toluene.

In some examples, the systems and methods described herein can be used to separate a binary system comprising acrylonitrile and at least one of isopropyl alcohol and benzene.

In certain examples, the systems and methods described herein can be used to separate a binary system comprising pyruvic acid and at least one of propionic acid, benzene, toluene, o-xylene, ethylbenzene, mesitylene or propylbenzene.

In some examples, the systems and methods described herein can be used to separate a binary system comprising methyl chloroacetate and at least one of isobutyl alcohol, cyclopentanol, amyl alcohol, isoamyl alcohol, ethylbenzene, m-xylene or p-xylene.

In certain embodiments, the systems and methods described herein can be used to separate a binary system comprising propionitrile and at least one of propyl alcohol, n-hexane or ethylbenzene.

In certain examples, the systems and methods described herein can be used to separate a binary system comprising acetone and at least one of methyl acetate, diethylamine, pyridine, cyclopentane, n-pentane, benzene, cyclohexane, n-hexane, isopropyl ether or n-heptane.

In other examples, the systems and methods described herein can be used to separate a binary system comprising allyl alcohol and at least one of ethyl sulfide, pyridine, benzene, cyclohexane, n-hexane, methylcyclohexane, m-xylene, 2,5-dimethylhexane or n-octane.

In certain embodiments, the systems and methods described herein can be used to separate a binary system comprising ethyl formate and at least one of n-pentane, benzene, methylcyclopentane or n-hexane.

In some embodiments, the systems and methods described herein can be used to separate a binary system comprising methyl acetate and at least one of cyclopentane, benzene, cyclohexane, n-hexane, n-heptane, 2-methylhexane or 2,3-trimethylbutane.

In certain embodiments, the systems and methods described herein can be used to separate a binary system comprising propionic acid and at least one of pyridine, 2-picoline, chlorobenzene, benzene, o-xylene, p-xylene, n-hexane, n-heptane, n-octane, n-nonane, n-decane, n-undecane, propyl sulfide, quinolone, cumene, mesitylene, propylbenzene, camphene or alpha-pinene.

In certain examples, the systems and methods described herein can be used to separate a binary system comprising propionamide and at least one of p-bromochlorobenzene or p-dibromobenzene, iodobenzene, nitrobenzene, o-nitrophenol, phenol, p-bromotoluene, m-nitrotoluene, toluene, o-cresol, m-cresol, o-toluidine, m-toluidine, acetophenone, methyl salicylate, o-xylene, dimethylaniline, 3,4-xylidine, quinolone, indene, ethyl benzoate, cumene, 1-mesitylene, naphthalene, cymene, carvone, camphene, camphor, borneol, n-decane, 1-methylnaphthalene, 2-methylnaphthalene, n-undecane, acenaphthene, biphenyl, n-dodecane, fluorine or diphenylmethane.

In certain embodiments, the systems and methods described herein can be used to separate a binary system comprising ethyl carbamate and at least one of bromobenzene, iodobenzene, nitrobenzene, phenol, benzonitrile, anisole, 2,4-xylenol, n-octyl alcohol, isobutyl sulfide, indene, cumene, mesitylene, propylbenzene, pseudocumene, naphthalene, butylbenzene, camphene, limonene, camphor, 2-methylnaphthalene, amyl ether, isoamyl ether or methyl pelargonate.

In some examples, the systems and methods described herein can be used to separate a binary system comprising 1-nitropropane and at least one of propyl alcohol, n-butyl alcohol, isobutyl alcohol, n-heptane, ethylbenzene, n-octane or n-nonane.

In certain examples, the systems and methods described herein can be used to separate a binary system comprising propyl nitrite and at least one of n-pentane or cyclopentane.

In other examples, the systems and methods described herein can be used to separate a binary system comprising isopropyl alcohol and at least one of butylamine, n-pentane, fluorobenzene, benzene, cyclohexane, n-hexane, toluene, n-heptane, o-xylene or n-octane.

In certain embodiments, the systems and methods described herein can be used to separate a binary system comprising propyl alcohol and at least one of dioxane, butyl formate, chlorobenzene, fluorobenzene, benzene, cyclohexane, toluene, methylcyclohexane, n-heptane, styrene, o-xylene, m-xylene, p-xylene or n-octane.

In certain examples, the systems and methods described herein can be used to separate a binary system comprising glycerol and at least one of p-chloronitrobenzene, triethylene glycol, m-nitrotoluene, p-cresol, methyl salicylate, 3,4-xylenol, o-xylene, quinolone, ethyl salicylate, naphthalene, safrol, methyl phthalate, estragol, eugenol, propyl benzoate, carvone, 2-methylnaphthalene, acenaphthene, biphenyl, phenyl ether, 1,3,5-triethylbenzene, bornyl acetate, diphenylmethane, benzyl phenyl ether or benzyl ether.

In some embodiments, the systems and methods described herein can be used to separate a binary system comprising ethyl methyl sulfide and at least one of cyclohexane, methylcyclopentane, n-hexane or 2,2-dimethylpentane.

In certain examples, the systems and methods described herein can be used to separate a binary system comprising 1-propanethiol and at least one of thiophene, cyclohexane, 2,3-dimethylbutane, n-hexane, 2-methylpentane, isopropyl ether, 2,2-dimethylpentane or 2,2,3-trimethylbutane.

In some examples, the systems and methods described herein can be used to separate a binary system comprising perfluorobutyric acid and at least one of ethyl-benzene, m-xylene or p-xylene.

In additional examples, the systems and methods described herein can be used to separate a binary system comprising thiophene and at least one of benzene, cyclohexane, methylcyclopentane, n-hexane, 2,3-dimethylpentane, 2,4-dimethylpentane or n-heptane.

In some embodiments, the systems and methods described herein can be used to separate a binary system comprising pyrrol and at least one of chlorobenzene, isopropyl sulfide, propyl sulfide or toluene.

In certain examples, the systems and methods described herein can be used to separate a binary system comprising methyl pyruvate and at least one of isoamyl acetate or m-xylene.

In some embodiments, the systems and methods described herein can be used to separate a binary system comprising methyl oxalate and at least one of p-dichlorobenzene, pinacol, o-bromotoluene, butyl butyrate, ethyl caproate, indene, mesitylene, naphthalene, 2,7-dimethyloctane or 1,3,5-triethylbenzene.

In certain embodiments, the systems and methods described herein can be used to separate a binary system comprising ethyl bromoacetate and at least one of butyric acid, isobutyric acid, bromobenzene, cyclohexanol, o-chlorotoluene or propylbenzene.

In some examples, the systems and methods described herein can be used to separate a binary system comprising one of ethyl chloroacetate and at least one of isoamyl acetate, isoamyl alcohol, allyl sulfide, propyl butyrate, ethylbenzene, o-xylene, m-xylene or butyl ether.

In certain examples, the systems and methods described herein can be used to separate a binary system comprising butyronitrile and at least one of n-butyl alcohol, toluene or methylcyclohexane.

In some examples, the systems and methods described herein can be used to separate a binary system comprising isobutyronitrile and at least one of benzene, methylcyclohexane or n-heptane.

In certain embodiments, the systems and methods described herein can be used to separate a binary system comprising 2-Butanone and at least one of methyl propionate, ethyl acetate, 1-chlorobutane, butyl nitrite, tert-butyl alcohol, butylamine, fluorobenzene, benzene, cyclohexane, n-hexane, n-heptane or 2,5-dimethylhexane.

In certain examples, the systems and methods described herein can be used to separate a binary system comprising butyraldehyde and at least one of benzene or n-hexane.

In some examples, the systems and methods described herein can be used to separate a binary system comprising butyric acid and at least one of iodobutane, 2-furaldehyde, pyridine, propyl chloroacetate, isoamyl nitrate, p-dichlorobenzene, chlorobenzene, o-bromotoluene, m-bromotoluene, p-bromotoluene, anisole, n-heptane, styrene, ethylbenzene, o-xylene, m-xylene, p-xylene, indene, cumene, mesitylene, propylbenzene, pseudocumene, naphthalene, butylbenzene, cymene, camphene or n-undecane.

In certain embodiments, the systems and methods described herein can be used to separate a binary system comprising dioxane and at least one of ethyl acetate, 1-bromobutane, pyridine, piperidine, tert-amyl alcohol, benzene, cyclohexane, ethyl borate, toluene or n-heptane.

In certain examples, the systems and methods described herein can be used to separate a binary system comprising ethyl acetate and at least one of butyl nitrite, isobutyl nitrite, tert-butyl alcohol, benzene, cyclohexane, methylcyclopentane, n-hexane or methylcyclohexane.

In some embodiments, the systems and methods described herein can be used to separate a binary system comprising isobutyric acid and at least one of iodobutane, ethyl pyruvate, bromobenzene, chlorobenzene, phenol, 1-bromohexane, o-bromotoluene, toluene, anisole, styrene, o-xylene, m-xylene, p-xylene, cumene, propylbenzene, pseudocumene, cymene, camphene, d-limonene, 2,7-dimethyloctane or isoamyl ether.

In certain embodiments, the systems and methods described herein can be used to separate a binary system comprising methyl propionate and at least one of 1-chlorobutane, butyl nitrite, n-butyl alcohol, benzene, cyclohexane, methylcyclopentane, propyl ether or methylcyclohexane.

In some examples, the systems and methods described herein can be used to separate a binary system comprising propyl formate and at least one of 1-chlorobutane, butyl nitrite, tert-butyl alcohol, benzene, cyclohexane, n-hexane or n-heptane.

In certain examples, the systems and methods described herein can be used to separate a binary system comprising glycol monoacetate and at least one of phenol, m-bromotoluene, o-cresol, m-cresol, p-cresol, n-octyl alcohol, indene, naphthalene, amyl ether, isoamyl ether or 1,3,5-triethylbenzene.

In certain embodiments, the systems and methods described herein can be used to separate a binary system comprising methyl lactate and at least one of phenol, anisole, 4-heptanone, ethyl valerate, methyl caproate, m-xylene, p-xylene, n-octane, butyl ether, cumene, camphene or 2,7-dimethyloctane.

In certain examples, the systems and methods described herein can be used to separate a binary system comprising tetrahydrothiophene and at least one of pyridine, 1-methylpyrrol, ethylcyclohexane, 2-methylheptane or n-octane.

In certain embodiments, the systems and methods described herein can be used to separate a binary system comprising butyl nitrite and at least one of benzene, cyclohexane, n-hexane, methylcyclohexane or n-heptane.

In certain examples, the systems and methods described herein can be used to separate a binary system comprising isobutyl nitrite and at least one of benzene, cyclohexane, methylcyclopentane or n-hexane.

In certain embodiments, the systems and methods described herein can be used to separate a binary system comprising isobutyl nitrate and at least one of n-butyl alcohol, isobutyl alcohol, chlorobenzene, propyl sulfide, toluene or ethylbenzene.

In some examples, the systems and methods described herein can be used to separate a binary system comprising n-butyl alcohol and at least one of pyridine, butyl formate, ethyl carbonate, chlorobenzene, fluorobenzene, benzene, 2-picoline, cyclohexene, cyclohexane, hexaldehyde, ethyl isobutyrate, isoamyl formate, isobutyl acetate, methyl isovalerate, paraldehyde, n-hexane, acetal, isopropyl sulfide, ethyl borate, toluene, methylcyclohexane, n-heptane, ethylbenzene, o-xylene, m-xylene, p-xylene, n-octane, butyl ether, isobutyl ether, n-nonane or 2,7-dimethylocatine.

In certain examples, the systems and methods described herein can be used to separate a binary system comprising sec-butyl alcohol and at least one of butyl formate, ethyl propionate, benzene, cyclohexane, propyl ether, toluene, methylcyclohexane, n-heptane or isooctane.

In some embodiments, the systems and methods described herein can be used to separate a binary system comprising tert-butyl alcohol and at least one of ethyl sulfide, fluorobenzene, benzene, cyclohexane, methylcyclopentane, n-hexane, isopropyl ether, propyl ether, toluene, methylcyclohexane, n-heptane, p-xylene or 2,5-dimethylhexane.

In certain embodiments, the systems and methods described herein can be used to separate a binary system comprising ethyl ether and at least one of isoprene, n-pentane, benzene or n-hexane.

In certain examples, the systems and methods described herein can be used to separate a binary system comprising isobutyl alcohol and at least one of 2-pentanone, 3-pentanone, butyl formate, methyl butyrate, propyl acetate, n-pentane, -chlorobenzene, fluorobenzene, benzene, cyclohexene, cyclohexane, methylcyclopentane, isobutyl vinyl ether, ethyl isobutyrate, n-hexane, propyl ether, acetal, isopropyl sulfide, toluene, methylcyclohexane, n-heptane, ethylbenzene, p-xylene, 1 3-dlmethylcyclohexane, 2,5-dimethylhexane, 2,2,4-trimethylpentane or butyl ether.

In some embodiments, the systems and methods described herein can be used to separate a binary system comprising 2-ethoxyethanol and at least one of toluene, methylcyclohexane, propyl butyrate, n-heptane, styrene, ethylbenzene, p-xylene, n-octane, cumene, propylbenzene or camphene.

In certain examples, the systems and methods described herein can be used to separate a binary system comprising methyl propyl ether and at least one of 2-methyl-2-butene and one of n-pentane or isoprene.

In some examples, the systems and methods described herein can be used to separate a binary system comprising diethylene glycol and at least one of p-dibromobenzene, nitrobenzene, o-nitrophenol, pyrocatechol, m-nitrotoluene, methyl salicylate, p-cresol, ethyl fumarate, quinolone, benzyl acetate, naphthalene, isosafrol, safrol, methyl phthalate, thymol, 1-methylnaphthalene, 2-methylnaphthalene, biphenyl, acenaphthene, 1,3,5-triethylbenzene, bornyl acetate, fluorene, diphenylmethane or benzyl phenyl ether.

In certain embodiments, the systems and methods described herein can be used to separate a binary system comprising 1-butanethiol and at least one of benzene, pyridine, n-heptane, 2-methylexane, 3-methylhexane or 2,5-dimethylhexane.

In some examples, the systems and methods described herein can be used to separate a binary system comprising isopropyl methyl sulfide and at least one of cyclohexane, methylcyclohexane or 2,4-dimethylpentane.

In certain examples, the systems and methods described herein can be used to separate a binary system comprising methyl propyl sulfide and at least one of ethylcyclopentane, methylcyclopentane or 3-methyhexane.

In some embodiments, the systems and methods described herein can be used to separate a binary system comprising 2-furaldehyde and at least one of n-heptane, ethylbenzene, o-xylene, m-xylene, p-xylene, cumene, mesitylene, pseudocumene, propylbenzene, cymene, camphene or cineol.

In certain examples, the systems and methods described herein can be used to separate a binary system comprising pyridine and at least one of piperidine, phenol, toluene, n-heptane, -octane, n-nonane or n-decane.

In certain embodiments, the systems and methods described herein can be used to separate a binary system comprising 2-methylthiophene and at least one of n-heptane, 2-methylheptane, 2,2-dimethylhexane or 2,5-dimethylhexane.

In certain examples, the systems and methods described herein can be used to separate a binary system comprising 3-methylthiophene and at least one of ethylcyclopentane, n-octane, 2-methylheptane or 2,5-dimethylhexane.

In some embodiments, the systems and methods described herein can be used to separate a binary system comprising ethyl pyruvate and at least one of bromobenzene, m-xylene or cumene.

In additional embodiments, the systems and methods described herein can be used to separate a binary system comprising levulinic acid and at least one of m-nitrotoluene, p-nitrotoluene, methyl salicylate, 3,4-xylenol, ethyl salicylate, naphthalene, safrol, 1-methylnaphthalene, 2-methylnaphthalene, isobutyl benzoate or 1,3,5-triethylbenzene.

In certain embodiments, the systems and methods described herein can be used to separate a binary system comprising methyl acetoacetate and at least one of isobutyl sulfide, mesitylene, cymene, camphene or isoamyl ether.

In some examples, the systems and methods described herein can be used to separate a binary system comprising methyl malonate and at least one of acetophenone, naphthalene, butylbenzene, cymene, camphene or d-limonene.

In certain embodiments, the systems and methods described herein can be used to separate a binary system comprising 2-pentanone and at least one of methyl butyrate, toluene, methylcyclohexane or n-heptane.

In certain examples, the systems and methods described herein can be used to separate a binary system comprising butyl formate and at least one of tert-amyl alcohol, benzene, pinacolone, methylcyclohexane or n-heptane.

In other embodiments, the systems and methods described herein can be used to separate a binary system comprising isovaleric acid and at least one of ethyl acetoacetate, ethyl oxalate, o-xylene, butyl sulfide, indene, cumene, mesitylene, pseudocumene, naphthalene, butylbenzene, cymene, camphene, cineol, n-decane or n-tridecane.

In certain examples, the systems and methods described herein can be used to separate a binary system comprising methyl butyrate and at least one of methylcyclohexane, n-heptane or n-octane.

In certain embodiments, the systems and methods described herein can be used to separate a binary system comprising propyl acetate and at least one of tert-amyl alcohol, benzene, cyclohexane, n-hexane or acetal.

In some embodiments, the systems and methods described herein can be used to separate a binary system comprising valeric acid and at least one of phenol, indene, mesitylene, naphthalene, cymene, camphene, amyl ether or isoamyl ether.

In some examples, the systems and methods described herein can be used to separate a binary system comprising ethyl lactate and at least one of toluene, o-xylene, p-xylene, cumene, mesitylene, pseudocumene or camphene.

In certain examples, the systems and methods described herein can be used to separate a binary system comprising n-amyl alcohol and at least one of benzene, phenol, amyl formate, ethylbenzene or p-xylene.

In some embodiments, the systems and methods described herein can be used to separate a binary system comprising isoamyl alcohol and at least one of bromobenzene, butyl acetate, paraldehyde, o-fluorotoluene, toluene, n-heptane, ethylbenzene, n-octane, butyl ether, cumene or camphene.

In certain embodiments, the systems and methods described herein can be used to separate a binary system comprising nitrobenzene and at least one of aniline, methyl maleate, benzyl alcohol, 3,4-xylenol, ethyl benzoate, camphor, borneol, 1,3,5-triethylbenzene or ethyl bornyl ether.

In certain examples, the systems and methods described herein can be used to separate a binary system comprising iodobenzene and at least one of nitrobenzene, phenol, ethyl oxalate, caproic acid, isocaproic acid, benzyl alcohol, p-cresol, o-toluidine, isobutyl lactate, indene, isoamyl butyrate or butylbenzene.

In certain embodiments, the systems and methods described herein can be used to separate a binary system comprising benzene and at least one of aniline, cyclohexene, cyclohexane, methylcyclopentane, n-hexane, 2,2-dimethylpentane, 2,3-dimethylpentane, 2,4-dimethylpentane, n-heptane or 2,2,4-trimethylpentane.

In some examples, the systems and methods described herein can be used to separate a binary system comprising phenol and at least one of aniline, 2-picoline, 3-picoline, 4-picoline, ethylene diacetate, benzaldehyde, o-cresol, 2,4-lutidine, 2,6-lutidine, o-toluidine, 2,4,6-collidine, n-octyl alcohol, sec-octyl alcohol, indene, mesitylene, pseudocumene, naphthalene, butylbenzene, camphene, n-decane, 2,7-dimethyloctane, amyl ether, isoamyl ether, isoamyl sulfide, 1,3,5-triethylbenzene or n-tridecane.

In some embodiments, the systems and methods described herein can be used to separate a binary system comprising pyrocatechol and at least one of indole, o-phenetidine, p-phenetidine, quinoline, naphthalene, quinaldine, safrole, isosafrole, eugenol, carvone, thymol, 1-methylnaphthalene, 2-methylnaphthalene, acenaphthene, biphenyl, phenyl ether, 1,3,5-triethylbenzene, fluorine, diphenyl methane, n-tridecane or 1,2-diphenylethane.

In additional embodiments, the systems and methods described herein can be used to separate a binary system comprising resorcinol and at least one of naphthalene, 1-naphthol, 2-naphthol, methyl phthalate, 1-methylnaphthalene, 2-methylnaphthalene, p-tert-amylphenol, acenaphthene, biphenyl, phenyl ether, fluorine, n-tridecane, stilbene or 1,2-diphenylethane.

In certain embodiments, the systems and methods described herein can be used to separate a binary system comprising pyrogallol and at least one of 2-naphthol, acenaphthene or biphenyl.

In some examples, the systems and methods described herein can be used to separate a binary system comprising aniline and at least one of o-cresol, n-octyl alcohol, o-xylene, indene, mesitylene, pseudocumene, naphthalene, butylbenzene, n-nonane, n-decane, amyl ether, isoamyl ether, 2-methylnaphthalene, n-undecane, 1,3,5-triethylbenzene, n-dodecane, n-tridecane or n-tetradecane.

In certain examples, the systems and methods described herein can be used to separate a binary system comprising 2-picoline and at least one of n-octane, n-nonane or n-decane.

In some embodiments, the systems and methods described herein can be used to separate a binary system comprising 3-picoline and at least one of allyl sulfide or 2,6-lutidine.

In certain embodiments, the systems and methods described herein can be used to separate a binary system comprising o-phenylenediamine and at least one of isosafrole, isafrole, biphenyl, phenyl ether, diphenylmethane or 1,2-diphenylethane.

In certain examples, the systems and methods described herein can be used to separate a binary system comprising methyl fumarate and at least one of m-bromotoluene, o-cresol, m-cresol, benzyl ethyl ether, naphthalene or dipentene.

In some examples, the systems and methods described herein can be used to separate a binary system comprising methyl maleate and at least one of caproic acid, o-cresol, m-cresol, p-cresol, naphthalene, borneol or isoamyl sulfide.

In some embodiments, the systems and methods described herein can be used to separate a binary system comprising cyclohexanone and at least one of n-hexyl alcohol, cumene, camphene or 2,7-dimethyloctane.

In certain embodiments, the systems and methods described herein can be used to separate a binary system comprising ethyl acetoacetate and at least one of phenetole, isobutyl sulfide, indene, propylbenzene, pseudocumene, butylbenzene, cymene, camphene, dipentene, d-limonene, 2,7-dimethyloctane or amyl ether.

In certain examples, the systems and methods described herein can be used to separate a binary system comprising ethylidene diacetate and at least one of phenetole, butylbutyrate, ethyl caproate, sec-octyl alcohol, cineole or isoamyl ether.

In some examples, the systems and methods described herein can be used to separate a binary system comprising ethyl oxalate and at least one of o-cresol, camphene, 2,7-dimethyloctane, amyl ether or isoamyl ether.

In some embodiments, the systems and methods described herein can be used to separate a binary system comprising glycol diacetate or o-cresol.

In certain embodiments, the systems and methods described herein can be used to separate a binary system comprising capronitrile and at least one of cumene or camphene.

In certain examples, the systems and methods described herein can be used to separate a binary system comprising cyclohexanol and at least one of o-xylene, m-xylene, indene, propylbenzene, naphthalene, cymene, camphene or cineole.

In some examples, the systems and methods described herein can be used to separate a binary system comprising butyl acetate and at least one of paraldehyde, n-octane or butyl ether.

In some embodiments, the systems and methods described herein can be used to separate a binary system comprising caproic acid and at least one of m-cresol, guaiacol, acetophenone, naphthalene, 1-methylnaphthalene, 2-methylnaphthalene or 1,3,5-triethylbenzene.

In certain examples, the systems and methods described herein can be used to separate a binary system comprising isoamyl formate and at least one of paraldehyde, ethylbenzene or isobutyl ether.

In certain embodiments, the systems and methods described herein can be used to separate a binary system comprising propyl propionate and at least one of toluene or n-octane.

In certain examples, the systems and methods described herein can be used to separate a binary system comprising propyl lactate and at least one of o-cresol, isobutyl sulfide, mesitylene or isoamyl ether.

In some examples, the systems and methods described herein can be used to separate a binary system comprising isopropyl lactate and at least one of o-cresol, mesitylene or camphene.

In certain examples, the systems and methods described herein can be used to separate a binary system comprising n-hexyl alcohol and at least one of o-cresol, anisole, m-xylene, cumene, mesitylene, pesudocumene, or propylbenzene.

In other examples, the systems and methods described herein can be used to separate a binary system comprising a acetal and at least one of methylcyclohexane, n-heptane, 2,5-dimethylhexane or n-octane.

In some embodiments, the systems and methods described herein can be used to separate a binary system comprising 2-butoxyethanol and at least one of benzaldehyde, o-cresol, phenetole, isobutyl sulfide, mesitylene, butylbenzene, camphene, dipentene or cineole.

In certain embodiments, the systems and methods described herein can be used to separate a binary system comprising pinacol and at least one of o-cresol, p-cresol, n-octane, pseudocumene, propylbenzene, naphthalene, p-cymene, cineole or isoamyl ether.

In certain examples, the systems and methods described herein can be used to separate a binary system comprising dipropylene glycol and at least one of p-cresol, methyl salicylate, isosafrole, safrole or 2-methylnaphthalene.

In certain examples, the systems and methods described herein can be used to separate a binary system comprising triethylene glycol and at least one of methyl phthalate, 1-methylnaphthalene, acenaphthene, biphenyl, fluorine, phenyl benzoate, diphenylmethane, stilbene or 1,2-diphenylethane.

In certain embodiments, the systems and methods described herein can be used to separate a binary system comprising benzonitrile and at least one of o-cresol, m-cresol, p-cresol, o-toluidine, isoamyl butyrate, cineole, amyl ether or isoamyl ether.

In certain examples, the systems and methods described herein can be used to separate a binary system comprising benzaldehyde and at least one of o-cresol, p-cresol, naphthalene, p-cymene, d-limonene, camphene or isoamyl ether.

In some embodiments, the systems and methods described herein can be used to separate a binary system comprising benzoic acid and at least one of p-nitrotoluene, 3,4-xylenol, propyl succinate, naphthalene, 1-methylnaphthalene, 2-methylnaphthalene, biphenyl, phenyl ether, fluorine, diphenylmethane or 1,2-diphenylethane.

In some examples, the systems and methods described herein can be used to separate a binary system comprising o-nitrotoluene and at least one of benzyl alcohol, methyl salicylate, 3,4-xylenol, 2,4-xylidine, naphthalene, diethylaniline, geraniol, menthol, n-decyl alcohol, 2-methylnaphthalene or bornyl acetate.

In certain embodiments, the systems and methods described herein can be used to separate a binary system comprising p-nitrotoluene and at least one of quinolone, safrole, geraniol, n-decyl alcohol or bornyl acetate.

In certain examples, the systems and methods described herein can be used to separate a binary system comprising toluene and at least one of 2,6-lutidine, ethylcyclopentane, n-heptane, 2,5-dimethylhexane, 2-methylheptane or 2,3,4-trimethylpentane.

In some embodiments, the systems and methods described herein can be used to separate a binary system comprising benzyl alcohol and at least one of o-cresol, m-cresol, p-cresol, methylaniline, o-toluidine, 3,4-xylenol, dimethylaniline, ethylaniline, 2,4-xylidine, naphthalene, diethylaniline, d-limonene, borneol or 1,3,5-triethylbenzene.

In some examples, the systems and methods described herein can be used to separate a binary system comprising o-cresol and at least one of benzylamine, phenyl acetate, 2,4,6-collidine, n-octyl alcohol, butyl sulfide, indene, naphthalene, terpinene, terpinolene, thymene or camphor.

In certain examples, the systems and methods described herein can be used to separate a binary system comprising m-cresol and at least one of o-toluidine, m-toluidine, p-toluidine, phenyl acetate, 2,4,6-collidine, isoamyl lactate, n-octyl alcohol, propiophenone, phorone, naphthalene, camphor or 1,3,5-triethylbenzene.

In certain embodiments, the systems and methods described herein can be used to separate a binary system comprising p-cresol and at least one of o-toluidine, m-toluidine, p-toluidine, o-anisidine, acetophenone, benzyl formate, methyl benzoate, phenyl acetate, isoamyl lactate, n-octyl alcohol, camphor or ethyl caprylate.

In certain examples, the systems and methods described herein can be used to separate a binary system comprising gualacol and at least one of acetophenone, m-toluidine, ethylaniline or ethyl caprylate.

In some examples, the systems and methods described herein can be used to separate a binary system comprising 2,4-lutidine and at least one of n-nonane or n-undecane.

In some embodiments, the systems and methods described herein can be used to separate a binary system comprising methylaniline and at least one of n-octyl alcohol or d-limonene.

In certain examples, the systems and methods described herein can be used to separate a binary system comprising o-toluidine and at least one of acetophenone, n-octyl alcohol, n-decane, n-undecane, n-dodecane or n-tridecane.

In certain embodiments, the systems and methods described herein can be used to separate a binary system comprising o-anisidine and at least one of naphthalene, 2-methylnaphthalene or 1,3,5-triethylbenzene.

In certain examples, the systems and methods described herein can be used to separate a binary system comprising enanthic acid and at least one of ethyl fumarate, ethyl maleate, ethyl succinate, propiophenone, naphthalene, biphenyl or 1,3,5-triethylbenzene.

In some examples, the systems and methods described herein can be used to separate a binary system comprising n-heptyl alcohol and at least one of benzyl methyl ether, p-methylanisole, phenetole, p-cymene or isoamyl ether.

In some embodiments, the systems and methods described herein can be used to separate a binary system comprising indole and at least one of carvacrol or p-tert-amylphenol.

In some examples, the systems and methods described herein can be used to separate a binary system comprising acetophenone and at least one of p-ethylphenol, 2,4-xylenol, 3,4-xylenol, dimethylaniline, ethylaniline, 2,4-xylidine, n-octyl alcohol, naphthalene or 1,3,5-triethylbenzene.

In some embodiments, the systems and methods described herein can be used to separate a binary system comprising phenyl acetate and at least one of 2,4-xylenol, n-octyl alcohol, indene, naphthalene, thymine or linalool.

In certain embodiments, the systems and methods described herein can be used to separate a binary system comprising methyl salicylate and at least one of phenethyl alcohol, 3,4-xylenol, ethyl maleate, quinolone, geraniol, menthol or n-tridecane.

In some examples, the systems and methods described herein can be used to separate a binary system comprising ethylbenzene and at least one of ethylcyclohexane, n-octane or n-nonane.

In some embodiments, the systems and methods described herein can be used to separate a binary system comprising p-ethylphenol and at least one of ethyl fumarate, ethyl maleate, p-methylacetophenone, benzyl acetate, ethyl benzoate, naphthalene, diethylaniline or 1,3,5-triethylbenzene.

In certain examples, the systems and methods described herein can be used to separate a binary system comprising p-methylanisole and at least one of sec-octyl alcohol, pseudocumene, butyl isovalerate, butylbenzene, cineole or isoamyl ether.

In certain embodiments, the systems and methods described herein can be used to separate a binary system comprising phenethyl alcohol and at least one of 3,4-xylenol, 2,4-xylidine, naphthalene, diethylaniline, borneol, menthol, 1-methylnaphthalene or biphenyl.

In some examples, the systems and methods described herein can be used to separate a binary system comprising 2,4-xylenol and at least one of ethyl fumarate, quinoline, p-methylacetophenone, propiophenone, benzyl acetate, or camphor.

In some embodiments, the systems and methods described herein can be used to separate a binary system comprising 3,4-xylenol and at least one of o-phenetidine, ethyl fumarate, ethyl maleale, quinoline, p-methylacetophenone, propiophenone, naphthalene, diethylaniline, camphor or n-tridecane.

In certain examples, the systems and methods described herein can be used to separate a binary system comprising ethylaniline and at least one of n-octyl alcohol, naphthalene or camphor.

In certain embodiments, the systems and methods described herein can be used to separate a binary system comprising 2,4-xylidine and at least one of menthol, n-undecane, n-dodecane, n-tridecane or n-tetradecane.

In certain examples, the systems and methods described herein can be used to separate a binary system comprising o-phenetidine and at least one of ethyl salicylate, naphthalene, safrole, anethole, carvacrol, thymol or 2-methylnaphthalene.

In some embodiments, the systems and methods described herein can be used to separate a binary system comprising p-Phenetidine and at least one of safrole, isosafrole, 1-methylnaphthalene, 2-methylnaphthalene, biphenyl or phenyl ether.

In some examples, the systems and methods described herein can be used to separate a binary system comprising ethyl fumarate and at least one of naphthalene, thymol or menthol.

In other embodiments, the systems and methods described herein can be used to separate a binary system comprising ethyl maleate and at least one of p-methylacetophenone, naphthalene or thymol.

In other examples, the systems and methods described herein can be used to separate a binary system comprising ethyl succinate and at least one of propiophenone, naphthalene or 2-methylnaphthalene.

In some examples, the systems and methods described herein can be used to separate a binary system comprising caprylic acid and at least one of naphthalene, carvacrol, 1-methylnaphthalene or 2-methylnaphthalene.

In some embodiments, the systems and methods described herein can be used to separate a binary system comprising propyl isovalerate and at least one of cumene, propylbenzene, camphene or nopinene.

In certain examples, the systems and methods described herein can be used to separate a binary system comprising sec-octyl alcohol and at least one of butylbenzene, p-cymene, thymene, cineole or amyl ether.

In certain embodiments, the systems and methods described herein can be used to separate a binary system comprising quinolone and at least one of mesitol, safrole, carvacrol, thymol, 1-methylnaphthalene, 2-methylnaphthalene, p-tert-amylphenol or biphenyl.

In certain examples, the systems and methods described herein can be used to separate a binary system comprising p-methylacetophenone and at least one of thymol, geraniol citronellol, 2-methylnaphthalene or bornyl acetate.

In some examples, the systems and methods described herein can be used to separate a binary system comprising propiophenone and at least one of benzyl acetate, borneol or 1,3,5-triethylbenzene.

In some embodiments, the systems and methods described herein can be used to separate a binary system comprising ethylsalicylate and at least one of safrole, geraniol, n-decyl alcohol or 2-methylnaphthalene.

In certain examples, the systems and methods described herein can be used to separate a binary system comprising cumene and n-nonane.

In certain embodiments, the systems and methods described herein can be used to separate a binary system comprising mesitylene and at least one of propylbenzene, camphene or 2,7-dimethyloctane.

In some examples, the systems and methods described herein can be used to separate a binary system comprising propylbenzene and camphene.

In certain examples, the systems and methods described herein can be used to separate a binary system comprising pseudocumene and at least one of p-cymene or n-decane.

In certain embodiments, the systems and methods described herein can be used to separate a binary system comprising mesitol and at least one of naphthalene or 1,3,5-triethylbenzene.

In some embodiments, the systems and methods described herein can be used to separate a binary system comprising 3-phenyipropanol and at least one of naphthalene, safrole, anethole, thymol or biphenyl.

In some examples, the systems and methods described herein can be used to separate a binary system comprising pelargonic acid and at least one of naphthalene, isosafrole, eugenol, thymol, 1-methylnaphthalene, 2-methylnaphthalene, biphenyl, phenyl ether, 1,3,5-triethylbenzene or diphenylmethane.

In certain embodiments, the systems and methods described herein can be used to separate a binary system comprising naphthalene and at least one of borneol, citronellol, menthol or n-tridecane.

In certain examples, the systems and methods described herein can be used to separate a binary system comprising quinaldine and at least one of safrole, carvacrol or thymol.

In some embodiments, the systems and methods described herein can be used to separate a binary system comprising methyl phthalate and at least one of acenapthene, biphenyl, diphenylmethane or 1,2-diphenylethane.

In certain embodiments, the systems and methods described herein can be used to separate a binary system comprising propyl benzoate and at least one of carvacrol, thymol or 2-methylnaphthalene.

In certain examples, the systems and methods described herein can be used to separate a binary system comprising p-cymene and at least one of dipentene, d-limonene or cineoloe.

In certain embodiments, the systems and methods described herein can be used to separate a binary system comprising carvacrol and at least one of carvenone, menthenone, propyl succinate, n-decyl alcohol, isobutyl benzoate, biphenyl or bornyl acetate.

In some examples, the systems and methods described herein can be used to separate a binary system comprising carvone and at least one of thymol, geraniol, n-decyl alcohol or 2-methylnaphthalene.

In some embodiments, the systems and methods described herein can be used to separate a binary system comprising thymol and at least one of carvenone, pulegone, -geraniol, menthone, 2-methylnaphthalene, isobutyl benzoate, 1,3,5-triethylbenzene or bornyl acetate.

In certain embodiments, the systems and methods described herein can be used to separate a binary system comprising camphene and at least one of dipentene or 2,7-dimethyloctane.

In certain examples, the systems and methods described herein can be used to separate a binary system comprising borneol and at least one of menthol and 1,3,5-triethylbenzene.

In some embodiments, the systems and methods described herein can be used to separate a binary system comprising menthol and at least one of 2-methylnaphthalene, terpineol methyl ether or 1,3,5-triethylbenzene.

In some examples, the systems and methods described herein can be used to separate a binary system comprising capric acid and at least one of 1-methylnaphthalene or diphenylmethane.

In certain examples, the systems and methods described herein can be used to separate a binary system comprising 1-methylnaphthalene and at least one of 2-methylnaphthalene, biphenyl, phenyl ether or diphenylmethane.

In certain embodiments, the systems and methods described herein can be used to separate a binary system comprising 2-methylnaphthalene and isobutyl benzoate.

In certain examples, the systems and methods described herein can be used to separate a binary system comprising p-tert-amylphenol and at least one of acenaphthene, fluorene or diphenylmethane.

In some embodiments, the systems and methods described herein can be used to separate a binary system comprising phenyl ether and at least one of isoamyl benzoate, isoamyl oxalate or diphenylmethane.

In some examples, the systems and methods described herein can be used to separate a binary system comprising isoamyl benzoate and at least one of isoamyl oxalate or diphenylmethane.

In certain examples, the systems and methods described herein can be used to separate a binary system comprising 1,3,5-triethylbenzene and at least one of bornyl acetate or bornyl ethyl ether.

In certain embodiments, the systems and methods described herein can be used to separate a binary system comprising isoamyl oxalate and at least one of diphenylmethane or 1,2-diphenylethane.

In other examples, the systems and methods described herein can be used to separate a binary system comprising phenyl benzoate and at least one of stilbene or benzyl ether.

In some embodiments, the systems and methods described herein can be used to separate a binary system comprising benzyl phenyl ether and 1,2-diphenylethane.

Illustrative binary systems where water is one of the solvents include combinations of water and at least one of hydrogen chloride, hydrogen bromide, hydrogen iodide, hydrogen fluoride, nitric acid, hydrogen peroxide, hydrazine, carbon tetrachloride, carbon disulfide, chloroform, formic acid, nitromethane, tetrachlorethylene, trichlorethylene, acetonitrile, acetic acid, acetamide, nitroethane, ethyl nitrate, ethyl alcohol, methyl sulfate, acrylonitrile, acrolein, acetone, allyl alcohol, propionaldehyde, ethyl formate, propionic acid, trioxane, 1-chloropropane, isopropyl alcohol, propyl alcohol, perfluorobutyric acid, crotonic acid, methyl acrylate, ethyl chloroacetate, butyronitrile, isobutyronitrile, ethyl vinyl ether, butyric acid, ethyl acetate, isopropyl formate, propyl formate, methyl lactate, butyl alcohol, sec-butyl alcohol, pyridine, furfuryl alcohol, furfurylamine, isoprene, cyclopentanone, allyl acetate, cyclopentanol, valeraldehyde, butyl formate, isopropyl acetate, isovaleric acid, methyl butyrate, methyl isobutyrate, valeric acid, piperidine, n-pentane, n-amyl alcohol, tert-amyl alcohol, 2-pentanol, N-methylbutylamine, chlorobenzene, nitrobenzene, benzene, phenol, aniline, 2-picoline, 3-picoline, 4-picoline, cyclohexene, ethyl crotonate, ethylene glycol diacetate, butyl chloroacetate, cyclohexane, amyl formate, butyl acetate, ethyl butyrate, isoamyl formate, isobutyl acetate, isopropyl propionate, propyl propionate, paraldehyde, n-hexane, butyl ethyl ether, n-hexyl alcohol, acetal, pinacol, toluene, anisole, benzyl alcohol, guaiacol, 2,6-lutidine, o-toluidine, 2-heptanone, 3-heptanone, 4-heptanone, ethyl valerate, isoamyl acetate, isobutyl propionate, n-heptane, benzyl formate, methyl benzoate, phenyl acetate, ethylbenzene, m-xylene, N-ethylaniline, 1-octene, hexyl acetate, isoamyl propionate, isobutyl butyrate, isobutyl isobutyrate, propyl isovalerate, n-octane, -isooctane, butyl ether, n-octyl alcohol, dibutylamine, quinoline, ethyl benzoate, cumene, mesitylene, triallylamine, isoamyl butyrate, isobutyl carbonate, n-nonane, naphthalene, methyl phthalate, nicotine, camphene, n-decane, n-undecane, o-phenyl phenol, phenyl ether, ethyl phthalate, isoamyl benzoate, n-dodecane, dihexylamine, and tributylamine.

In certain examples, the systems and methods described herein can be used to separate a ternary system comprising argon, nitrogen and oxygen.

In certain embodiments, the systems and methods described herein can be used to separate a ternary system comprising hydrogen bromide, water and chlorobenzene.

In some examples, the systems and methods described herein can be used to separate a ternary system comprising hydrogen cyanide, acetonitrile and acrolein.

In some embodiments, the systems and methods described herein can be used to separate a ternary system comprising chlorine trifluoride, hydrogen fluoride and uranium hexafluoride.

In certain examples, the systems and methods described herein can be used to separate a ternary system comprising hydrogen chloride, water and phenol.

In certain embodiments, the systems and methods described herein can be used to separate a ternary system comprising hydrogen chloride, water and chlorobenzene.

In certain examples, the systems and methods described herein can be used to separate a ternary system comprising hydrogen fluoride, fluosilicic acid and water.

In some examples, the systems and methods described herein can be used to separate a ternary system comprising silicon tetrafluoride, hexafluoroethane and ethane.

In some embodiments, the systems and methods described herein can be used to separate a ternary system comprising water, carbon tetrachloride and ethyl alcohol.

In certain examples, the systems and methods described herein can be used to separate a ternary system comprising water, carbon tetrachloride and allyl alcohol.

In certain embodiments, the systems and methods described herein can be used to separate a ternary system comprising water, carbon tetrachloride and sec-butyl alcohol.

In some examples, the systems and methods described herein can be used to separate a ternary system comprising water, carbon disulfide and ethyl alcohol.

In some embodiments, the systems and methods described herein can be used to separate a ternary system comprising water, carbon disulfide and dioxane.

In certain examples, the systems and methods described herein can be used to separate a ternary system comprising water, chloroform and formic acid.

In certain embodiments, the systems and methods described herein can be used to separate a ternary system comprising water, chloroform and methyl alcohol.

In certain examples, the systems and methods described herein can be used to separate a ternary system comprising water, chloroform and ethyl alcohol.

In some embodiments, the systems and methods described herein can be used to separate a ternary system comprising water, formic acid and propionic acid.

In some examples, the systems and methods described herein can be used to separate a ternary system comprising water, formic acid and butyric acid.

In other embodiments, the systems and methods described herein can be used to separate a ternary system comprising water, formic acid and isobutyric acid.

In certain examples, the systems and methods described herein can be used to separate a ternary system comprising water, formic acid and isovaleric acid.

In certain examples, the systems and methods described herein can be used to separate a ternary system comprising water, formic acid and valeric acid.

In other examples, the systems and methods described herein can be used to separate a ternary system comprising water, nitromethane and n-pentane/

In certain embodiments, the systems and methods described herein can be used to separate a ternary system comprising water, nitromethane and n-heptane.

In certain examples, the systems and methods described herein can be used to separate a ternary system comprising water, nitromethane and n-octane.

In some embodiments, the systems and methods described herein can be used to separate a ternary system comprising water, nitromethane and n-nonane.

In some examples, the systems and methods described herein can be used to separate a ternary system comprising water, nitromethane and n-decane.

In certain embodiments, the systems and methods described herein can be used to separate a ternary system comprising water, nitromethane and n-undecane.

In certain examples, the systems and methods described herein can be used to separate a ternary system comprising water, nitromethane and n-dodecane.

In some embodiments, the systems and methods described herein can be used to separate a ternary system comprising water, nitromethane and n-tridecane.

In certain embodiments, the systems and methods described herein can be used to separate a ternary system comprising water, methyl alcohol and ethyl alcohol.

In certain examples, the systems and methods described herein can be used to separate a ternary system comprising water, methyl alcohol and methyl chloroacetate.

In some examples, the systems and methods described herein can be used to separate a ternary system comprising water, methyl alcohol and methyl acetate.

In other examples, the systems and methods described herein can be used to separate a ternary system comprising water, methyl alcohol and isoprene.

In other embodiments, the systems and methods described herein can be used to separate a ternary system comprising water, tetrachloroethylene and n-propyl alcohol.

In certain examples, the systems and methods described herein can be used to separate a ternary system comprising water, trichloroethylene and acetonitrile.

In some examples, the systems and methods described herein can be used to separate a ternary system comprising water, trichloroethylene and ethyl alcohol.

In certain embodiments, the systems and methods described herein can be used to separate a ternary system comprising water, trichloroethylene and isopropyl alcohol.

In certain examples, the systems and methods described herein can be used to separate a ternary system comprising water, acetonitrile, and acetone.

In certain embodiments, the systems and methods described herein can be used to separate a ternary system comprising water, acetonitrile and ethyl alcohol.

In certain examples, the systems and methods described herein can be used to separate a ternary system comprising water, acetonitrile and diethylamine.

In some examples, the systems and methods described herein can be used to separate a ternary system comprising water, acetonitrile and benzene.

In some embodiments, the systems and methods described herein can be used to separate a ternary system comprising water, acetonitrile and triethylamine.

In certain embodiments, the systems and methods described herein can be used to separate a ternary system comprising water, acetic acid and toluene.

In certain examples, the systems and methods described herein can be used to separate a ternary system comprising water, nitroethane and n-hexane.

In some examples, the systems and methods described herein can be used to separate a ternary system comprising water, nitroethane and n-heptane.

In certain embodiments, the systems and methods described herein can be used to separate a ternary system comprising water, ethyl alcohol and acrylonitrile.

In certain examples, the systems and methods described herein can be used to separate a ternary system comprising water, ethyl alcohol and crotonaldehyde.

In other examples, the systems and methods described herein can be used to separate a ternary system comprising water, ethyl alcohol and ethyl acetate.

In other embodiments, the systems and methods described herein can be used to separate a ternary system comprising water, ethyl alcohol and butylamine.

In additional examples, the systems and methods described herein can be used to separate a ternary system comprising water, ethyl alcohol and butyl methyl ether.

In other embodiments, the systems and methods described herein can be used to separate a ternary system comprising water, ethyl alcohol and benzene.

In other examples, the systems and methods described herein can be used to separate a ternary system comprising water, ethyl alcohol and cyclohexane.

In certain examples, the systems and methods described herein can be used to separate a ternary system comprising water, ethyl alcohol and triethylamine.

In certain embodiments, the systems and methods described herein can be used to separate a ternary system comprising water, ethyl alcohol and toluene.

In some examples, the systems and methods described herein can be used to separate a ternary system comprising water, ethyl alcohol and n-hexane.

In other examples, the systems and methods described herein can be used to separate a ternary system comprising water, ethyl alcohol and n-heptane.

In certain examples, the systems and methods described herein can be used to separate a ternary system comprising water, acetone and isoprene.

In certain embodiments, the systems and methods described herein can be used to separate a ternary system comprising water, allyl alcohol and n-hexane.

In some examples, the systems and methods described herein can be used to separate a ternary system comprising water, isopropyl alcohol and butylamine.

In certain examples, the systems and methods described herein can be used to separate a ternary system comprising water, isopropyl alcohol and benzene.

In certain embodiments, the systems and methods described herein can be used to separate a ternary system comprising water, isopropyl alcohol and cyclohexane.

In some examples, the systems and methods described herein can be used to separate a ternary system comprising water, isopropyl alcohol and toluene.

In certain examples, the systems and methods described herein can be used to separate a ternary system comprising water, propyl alcohol and propyl acetate.

In certain embodiments, the systems and methods described herein can be used to separate a ternary system comprising water, propyl alcohol and benzene.

In some embodiments, the systems and methods described herein can be used to separate a ternary system comprising water, propyl alcohol and cyclohexane.

In some examples, the systems and methods described herein can be used to separate a ternary system comprising water, n-butyl alcohol and n-hexane.

In other examples, the systems and methods described herein can be used to separate a ternary system comprising water, n-butyl alcohol and n-heptane.

In other embodiments, the systems and methods described herein can be used to separate a ternary system comprising water, n-butyl alcohol and n-octane.

In certain examples, the systems and methods described herein can be used to separate a ternary system comprising water, n-butyl alcohol and n-nonane.

In certain embodiments, the systems and methods described herein can be used to separate a ternary system comprising water, n-butyl alcohol and butyl ether.

In some examples, the systems and methods described herein can be used to separate a ternary system comprising water, 2-butanone and cyclohexane.

In certain embodiments, the systems and methods described herein can be used to separate a ternary system comprising water, butyraldehyde and n-hexane.

In certain examples, the systems and methods described herein can be used to separate a ternary system comprising water, sec-butyl alcohol and cyclohexane.

In certain embodiments, the systems and methods described herein can be used to separate a ternary system comprising water, sec-butyl alcohol and isooctane.

In other examples, the systems and methods described herein can be used to separate a ternary system comprising water, tert-butyl alcohol and benzene.

In other embodiments, the systems and methods described herein can be used to separate a ternary system comprising water, tert-butyl alcohol and isoprene.

In some examples, the systems and methods described herein can be used to separate a ternary system comprising water, tert-butyl alcohol and cyclohexane.

In some embodiments, the systems and methods described herein can be used to separate a ternary system comprising water, isobutyl alcohol and benzene.

In certain examples, the systems and methods described herein can be used to separate a ternary system comprising water, isobutyl alcohol and toluene.

In certain instances, the systems and methods described herein can be used to separate a ternary system comprising water, ethyl acrylate and isopropyl ether.

In certain examples, the systems and methods described herein can be used to separate a ternary system comprising water, toluene and benzyl alcohol.

In some examples, the systems and methods described herein can be used to separate a ternary system comprising water, pyridine and benzene.

In certain embodiments, the systems and methods described herein can be used to separate a ternary system comprising water, pyridine and n-heptane.

In certain examples, the systems and methods described herein can be used to separate a ternary system comprising water, pyridine and n-octane.

In some embodiments, the systems and methods described herein can be used to separate a ternary system comprising water, pyridine and n-nonane.

In certain embodiments, the systems and methods described herein can be used to separate a ternary system comprising water, pyridine and n-decane.

In certain examples, the systems and methods described herein can be used to separate a ternary system comprising water, pyridine and n-undecane.

In other embodiments, the systems and methods described herein can be used to separate a ternary system comprising water, pyridine and n-dodecane.

In other examples, the systems and methods described herein can be used to separate a ternary system comprising water, isoamyl alcohol and isoamyl formate.

In certain embodiments, the systems and methods described herein can be used to separate a ternary system comprising water, isoamyl alcohol and isoamyl acetate.

In some examples, the systems and methods described herein can be used to separate a ternary system comprising water, 2-picoline and paraldehyde.

In certain examples, the systems and methods described herein can be used to separate a ternary system comprising carbon tetrachloride, methyl alcohol and benzene.

In some embodiments, the systems and methods described herein can be used to separate a ternary system comprising chloroform, formic acid and acetic acid.

In certain examples, the systems and methods described herein can be used to separate a ternary system comprising chloroform, methyl alcohol and acetone.

In other examples, the systems and methods described herein can be used to separate a ternary system comprising chloroform, ethyl alcohol and acetone.

In other embodiments, the systems and methods described herein can be used to separate a ternary system comprising chloroform, ethyl alcohol and n-hexane.

In some examples, the systems and methods described herein can be used to separate a ternary system comprising chloroform, acetone and n-hexane.

In certain examples, the systems and methods described herein can be used to separate a ternary system comprising chloroform, acetone and toluene.

In certain embodiments, the systems and methods described herein can be used to separate a ternary system comprising chloroform, ethyl formate and isopropyl bromide.

In some embodiments, the systems and methods described herein can be used to separate a ternary system comprising chloroform, 2-bromopropane and isopropyl formate.

In some examples, the systems and methods described herein can be used to separate a ternary system comprising methyl alcohol, acetone and methyl acetate.

In certain examples, the systems and methods described herein can be used to separate a ternary system comprising methyl alcohol, acetone and n-hexane.

In some embodiments, the systems and methods described herein can be used to separate a ternary system comprising methyl alcohol, methyl acetate and cyclohexane.

In certain embodiments, the systems and methods described herein can be used to separate a ternary system comprising methyl alcohol, methyl acetate and n-hexane.

In other examples, the systems and methods described herein can be used to separate a ternary system comprising methyl alcohol, benzene and cyclohexane.

In certain embodiments, the systems and methods described herein can be used to separate a ternary system comprising acetonitrile, ethyl alcohol and triethylamine.

In certain examples, the systems and methods described herein can be used to separate a ternary system comprising trichloroethytene, benzene and cyclohexane.

In some embodiments, the systems and methods described herein can be used to separate a ternary system comprising acetic acid, acetic anhydride and pyridine.

In some examples, the systems and methods described herein can be used to separate a ternary system comprising acetic acid, pyridine and n-heptane.

In some examples, the systems and methods described herein can be used to separate a ternary system comprising acetic acid, pyridine and n-octane.

In certain examples, the systems and methods described herein can be used to separate a ternary system comprising acetic acid, pyridine and n-nonane.

In some examples, the systems and methods described herein can be used to separate a ternary system comprising acetic acid, pyridine and n-decane.

In certain examples, the systems and methods described herein can be used to separate a ternary system comprising acetic acid, pyridine and n-undecane.

In some examples, the systems and methods described herein can be used to separate a ternary system comprising acetic acid, pyridine and ethylbenzene.

In some examples, the systems and methods described herein can be used to separate a ternary system comprising acetic acid, pyridine and o-xylene.

In certain examples, the systems and methods described herein can be used to separate a ternary system comprising acetic acid, pyridine and p-xylene.

In certain embodiments, the systems and methods described herein can be used to separate a ternary system comprising acetic acid, isoamyl alcohol and isoamyl acetate.

In certain examples, the systems and methods described herein can be used to separate a ternary system comprising acetic acid, benzene and cyclohexane.

In some examples, the systems and methods described herein can be used to separate a ternary system comprising acetic acid, 2-picoline and n-octane.

In certain embodiments, the systems and methods described herein can be used to separate a ternary system comprising acetic acid, 2-picoline and n-nonane.

In certain examples, the systems and methods described herein can be used to separate a ternary system comprising acetic acid, 2-picoline and n-decane.

In some examples, the systems and methods described herein can be used to separate a ternary system comprising acetic acid, 2-picoline and n-undecane In other examples, the systems and methods described herein can be used to separate a ternary system comprising acetic acid, 2,6-lutidine and n-octane.

In other embodiments, the systems and methods described herein can be used to separate a ternary system comprising acetic acid, 2,6-lutidine and n-decane.

In certain embodiments, the systems and methods described herein can be used to separate a ternary system comprising acetic acid, 2,6-lutidine and n-undecane.

In certain examples, the systems and methods described herein can be used to separate a ternary system comprising acetic acid, ethylbenzene and n-nonane.

In certain embodiments, the systems and methods described herein can be used to separate a ternary system comprising acetic acid, acetic anhydride and methylene diacetate.

In other embodiments, the systems and methods described herein can be used to separate a ternary system comprising methyl formate, ethyl ether, and n-pentane.

In other examples, the systems and methods described herein can be used to separate a ternary system comprising nitroethane, p-dioxane and isobutyl alcohol.

In some embodiments, the systems and methods described herein can be used to separate a ternary system comprising ethyl alcohol, benzene and cyclohexane.

In some examples, the systems and methods described herein can be used to separate a ternary system comprising ethyl alcohol, benzene and n-hexane.

In other examples, the systems and methods described herein can be used to separate a ternary system comprising ethyl alcohol, aniline and toluene.

In certain examples, the systems and methods described herein can be used to separate a ternary system comprising ethyl alcohol, aniline and n-heptane.

In some embodiments, the systems and methods described herein can be used to separate a ternary system comprising ethyl alcohol, toluene and n-heptane.

In certain embodiments, the systems and methods described herein can be used to separate a ternary system comprising ethylene glycol, pyridine and phenol.

In certain examples, the systems and methods described herein can be used to separate a ternary system comprising ethylene glycol, phenol and 2-picoline.

In some examples, the systems and methods described herein can be used to separate a ternary system comprising ethylene glycol, phenol and 3-picoline.

In certain embodiments, the systems and methods described herein can be used to separate a ternary system comprising ethylene glycol, phenol and 2,6-lutidine.

In some embodiments, the systems and methods described herein can be used to separate a ternary system comprising ethylene glycol, phenol and 2,4,6-collidine.

In certain examples, the systems and methods described herein can be used to separate a ternary system comprising ethylene glycol, o-cresol and 2,4,6-collidine.

In some examples, the systems and methods described herein can be used to separate a ternary system comprising acetone, methyl acetate and n-hexane.

In certain embodiments, the systems and methods described herein can be used to separate a ternary system comprising acetone, 2-butanone and ethyl acetate.

In some examples, the systems and methods described herein can be used to separate a ternary system comprising acetone, benzene and cyclohexane.

In certain examples, the systems and methods described herein can be used to separate a ternary system comprising acetone, benzene and toluene.

In certain embodiments, the systems and methods described herein can be used to separate a ternary system comprising propionic acid, pyridine and n-undecane.

In other embodiments, the systems and methods described herein can be used to separate a ternary system comprising propionic acid, 2-picoline and n-octane.

In other examples, the systems and methods described herein can be used to separate a ternary system comprising propionic acid, 2-picoline and n-nonane.

In certain examples, the systems and methods described herein can be used to separate a ternary system comprising propionic acid, 2-picoline and n-decane.

In some examples, the systems and methods described herein can be used to separate a ternary system comprising propionic acid, 2-picoline and n-undecane.

In certain embodiments, the systems and methods described herein can be used to separate a ternary system comprising propionic acid, 2-picoline and n-dodecane.

In other embodiments, the systems and methods described herein can be used to separate a ternary system comprising isopropyl alcohol, benzene and cyclohexane.

In certain embodiments, the systems and methods described herein can be used to separate a ternary system comprising propyl alcohol, benzene and cyclohexane.

In other examples, the systems and methods described herein can be used to separate a ternary system comprising propyl alcohol, benzene and n-heptane.

In other embodiments, the systems and methods described herein can be used to separate a ternary system comprising 2-butanone, ethyl acetate and n-hexane.

In certain examples, the systems and methods described herein can be used to separate a ternary system comprising 2-butanone, benzene and cyclohexane.

In certain embodiments, the systems and methods described herein can be used to separate a ternary system comprising butyric acid, pyridine and n-undecane.

In some embodiments, the systems and methods described herein can be used to separate a ternary system comprising p-dioxane, isobutyl alcohol and toluene.

In certain examples, the systems and methods described herein can be used to separate a ternary system comprising n-butyl alcohol, pyridine and toluene.

In certain embodiments, the systems and methods described herein can be used to separate a ternary system comprising n-butyl alcohol, benzene and cyclohexane.

In other embodiments, the systems and methods described herein can be used to separate a ternary system comprising n-butyl alcohol, benzene and n-heptane.

In certain embodiments, the systems and methods described herein can be used to separate a ternary system comprising isobutyl alcohol, benzene and cyclohexane.

In some embodiments, the systems and methods described herein can be used to separate a ternary system comprising pyridine, isoamyl alcohol and toluene.

In certain examples, the systems and methods described herein can be used to separate a ternary system comprising phenol, aniline and n-tridecane.

In some embodiments, the systems and methods described herein can be used to separate a ternary system comprising phenol, ethylene diacetate and phenyl acetate.

In some examples, the systems and methods described herein can be used to separate a ternary system comprising phenol, 2,4-lutidine and n-undecane.

In certain examples, the systems and methods described herein can be used to separate a ternary system comprising ethylbenzene, pyridine and n-nonane.

In certain embodiments, the systems and methods described herein can be used to separate a ternary system comprising aniline, toluene and n-heptane.

In some embodiments, the systems and methods described herein can be used to separate a ternary system comprising aniline, benzyl alcohol and d-limonene.

In some examples, the systems and methods described herein can be used to separate a ternary system comprising aniline, sec-octyl alcohol and d-limonene.

In certain examples, the systems and methods described herein can be used to separate a ternary system comprising aniline, o-bromotoluene and sec-octyl alcohol.

In some embodiments, the systems and methods described herein can be used to separate a ternary system comprising propyl lactate, phenetole and menthene.

In some examples, the systems and methods described herein can be used to separate a ternary system comprising m-p-cresol (mixture), pyridine bases (mixture) and naphthalene.

In certain embodiments, the systems and methods described herein can be used to separate a ternary system comprising m-,p-cresol (mixture), pyridine bases (mixture) and naphthalene.

In certain examples, the systems and methods described herein can be used to separate a ternary system comprising m-,p-cresol (mixture), pyridine bases (mixture) and naphthalene.

In some embodiments, the systems and methods described herein can be used to separate a ternary system comprising m-cresol, 2,4,6-collidine and naphthalene.

In certain embodiments, the systems and methods described herein can be used to separate a ternary system comprising isobutyl lactate, sec-octyl alcohol and terpinene.

In certain examples, the systems and methods described herein can be used to separate a ternary system comprising ethylbenzene, isopropylbenzene and butylbenzene.

In certain examples, the systems and methods described herein can be used to separate a quaternary system comprising hydrocyanic acid, water, acrylonitrile and acrolein.

In some embodiments the systems and methods described herein can be used to separate a quaternary system comprising hydrocyanic acid, acetonitrile, acrytonitrile and acrolein.

In certain embodiments, the systems and methods described herein can be used to separate a quaternary system comprising water, formic acid, acetic acid and butyric acid.

In certain examples, the systems and methods described herein can be used to separate a quaternary system comprising water, nitromethane, tetrachloroethylene and n-propyl alcohol.

In some examples, the systems and methods described herein can be used to separate a quaternary system comprising water, nitromethane, tetrachloroethylene and n-octane.

In some embodiments, the systems and methods described herein can be used to separate a quaternary system comprising water, tetrachloroethylene, n-propyl alcohol and n-octane.

In other embodiments, the systems and methods described herein can be used to separate a quaternary system comprising water, nitromethane, n-propyl alcohol and n-octane.

In other examples, the systems and methods described herein can be used to separate a quaternary system comprising water, acetonitrile, ethyl alcohol and triethylamine.

In certain embodiments, the systems and methods described herein can be used to separate a quaternary system comprising water, ethyl alcohol, crotonaldehyde and ethyl acetate.

In certain examples, the systems and methods described herein can be used to separate a quaternary system comprising water, ethyl alcohol, benzene and cyclohexane.

In some embodiments, the systems and methods described herein can be used to separate a quaternary system comprising water, ethyl alcohol, benzene and n-hexane.

In certain embodiments, the systems and methods described herein can be used to separate a quaternary system comprising water, ethyl alcohol, benzene, and methylcyclohexane.

In certain examples, the systems and methods described herein can be used to separate a quaternary system water, ethyl alcohol, benzene and n-heptane.

In certain instances, the systems and methods described herein can be used to separate a quaternary system comprising water, ethyl alcohol, benzene and isooctane.

In other embodiments, the systems and methods described herein can be used to separate a quaternary system comprising water, 1-Chlorobutane, n-butyl alcohol and butyl ether.

In some examples, the systems and methods described herein can be used to separate a quaternary system comprising chloroform, methyl alcohol, methyl acetate and benzene.

In some embodiments, the systems and methods described herein can be used to separate a quaternary system comprising acetic acid, pyridine, ethylbenzene and n-nonane.

In other examples, the systems and methods described herein can be used to separate a quaternary system acetic acid, pyridine, p-xylene and n-nonane.

In certain examples, the systems and methods described herein can be used to separate a quaternary system comprising acetone, isopropyl alcohol, benzene and toluene.

In certain embodiments, the systems and methods described herein can be used to separate a quaternary system comprising acetone, benzene, cyclohexane and toluene.

In some examples, the systems and methods described herein can be used to separate a quaternary system comprising isopropyl alcohol, 2-butanone, benzene and cyclohexane.

In some embodiments, the systems and methods described herein can be used to separate a quinary system comprising water, nitromethane, tetrachloroethylene, n-propyl alcohol and n-octane.

In certain examples, the systems and methods described herein can be used to separate a quinary system comprising chloroform, methyl alcohol, acetone, methyl acetate and benzene.

In certain embodiments, a method of removing a solvent from an azeotropic forming solvent mixture comprising a first solvent and a second solvent, the method comprising providing an effective amount of a supercritical fluid stream to the azeotropic solvent mixture to remove at least 95% by weight or more of the first solvent from the azeotropic forming solvent mixture is provided.

In certain examples, the pressure and temperature of the supercritical fluid can be configured to provide a supercritical fluid stream that is miscible with azeotropic forming solvent mixture. In some embodiments, the method can include depressurizing the removed first solvent in the supercritical fluid stream to collect the removed solvent. In other embodiments, the removed solvent can be collected in a closed vessel or in an open vessel. If desired, the supercritical fluid can be recycled and reused in the separation process. The reused supercritical fluid can be dried prior to reuse. In other embodiments, the supercritical fluid stream may be provided back to the chamber for further removal of any residual solvent.

In certain embodiments, the method can include adding a carrier to the supercritical fluid stream to increase the amount of the first solvent recovered compared to the amount recovered using the same supercritical fluid without the carrier.

In some examples, a method of removing and reusing a solvent in a processing solvent stream exiting a processing reactor is described. In certain embodiments, the method comprises receiving the azeotropic forming solvent mixture in a chamber, exposing the azeotropic forming solvent mixture in the chamber to a supercritical fluid stream at an effective temperature and pressure to remove at least about 95% by weight or more of the first solvent from the azeotropic forming solvent mixture, collecting the removed first solvent in the supercritical fluid stream; and providing the collected, removed first solvent to the processing reactor.

In certain embodiments, a method of removing about 95% by weight or more of NMP from a solvent mixture comprising NMP and ethylene glycol in a chamber, the method comprising exposing the solvent mixture comprising the NMP and the ethylene glycol to a supercritical fluid stream of carbon dioxide at an effective temperature and pressure to remove about 95% by weight or more of the NMP from the solvent mixture comprising the NMP and ethylene glycol, and collecting the removed NMP in the supercritical fluid stream of carbon dioxide exiting the chamber is disclosed.

In certain embodiments, the method can include providing the supercritical fluid stream at an effective pressure to be miscible with the NMP. In other embodiments, the method can include depressurizing the removed NMP in the supercritical fluid stream to collect the removed NMP. In further embodiments, the removed NMP can be collected in a closed vessel or an open vessel.

In certain embodiments, the systems described herein can be used to separate a selected volume of a binary solvent system into individual components using 10% less energy, e.g., 10% less kiloWatts, than the energy used for the same binary solvent system in a distillation separation. In some embodiments, the binary solvent system can be separated into individual components using 20% less energy, 30% less energy, 40% less energy, 50% less energy, 60% less energy, 70% less energy, 75% less energy or even 80% less energy than the energy used for the same binary solvent system in a distillation separation. In some instances, such low energy input can be used to provide at least 95% by weight recovery of the solvent, based on the total weight of the solvent mixture feed.

In other embodiments, the systems described herein can be used to remove at least 15% by weight of one solvent from a binary solvent system in less than 5 seconds, less than 10 seconds, less than 15 seconds or less than 20 seconds or less than 30 seconds. In some embodiments at least 50% by weight of one solvent in a binary solvent system can be removed in less than 30 seconds, less than 45 seconds or less than 60 seconds. Depending on the overall total weight of the binary solvent system, more time may be used to achieve a desired separation amount from the binary solvent system. To reduce the overall separation time, the binary solvent system can be split into multiple different chambers and the removed solvent can be recombined at a later stage as described herein.

Compared to conventional distillation, the methods and systems provided herein result in substantial time savings while achieving increased recoveries of the solvent components.

In certain embodiments, the systems described herein can be used to separate solvents in a solvent mixture in about 1-30 seconds from switching on the system. Compared to conventional distillation systems that can take hours to be ready for separations, a substantial time advantage can be achieved using the systems described herein. In some embodiments, separation may be initiated within about 5 seconds, 10 seconds, 15 seconds, 20 seconds, 25 seconds or 30 seconds from switching the system on, more particularly within about 60 seconds from switching the system on, e.g., within about 2, 3, 4, 5, 6, 7, 8, 9, 10, 11, 12, 13, 14, 15, 20, 25, or 30 minutes from switching the system on.

Certain specific examples are described below to further illustrate some of the novel attributes and aspects of the technology described herein.

EXAMPLE 1

Figure 16:
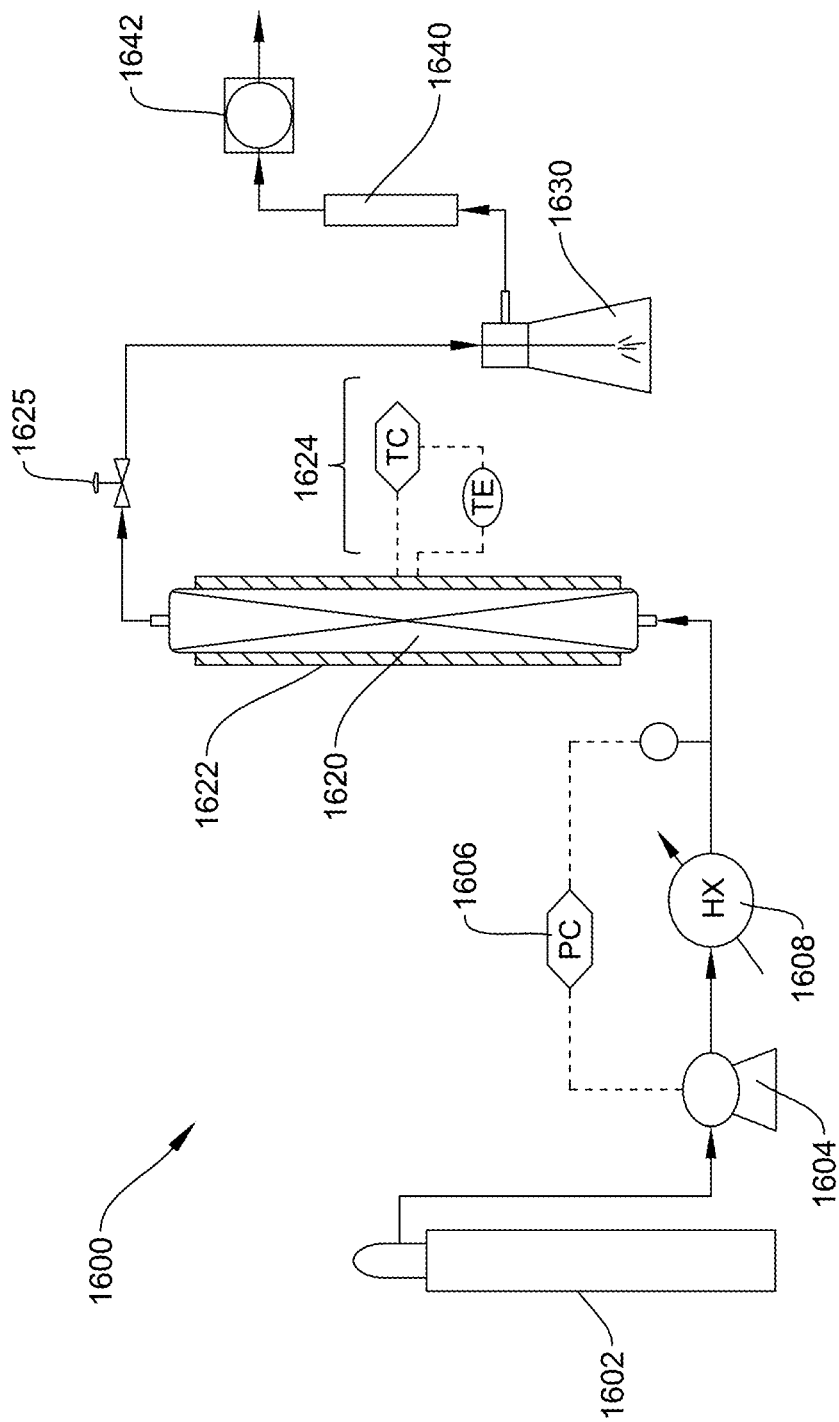
FIG. 16 is a schematic of a system used to separate a mixture of NMP and glycols in a solvent system, in accordance with certain examples.

A lab scale system was used to test the feasibility of separating an azeotropic forming solvent system. Referring to FIG. 16, the system 1600 included a chamber 1620 that was configured to receive a waste stream of solvent mixture. The volume of the chamber in this configuration was 250 mL. Supercritical carbon dioxide was provided from a carbon dioxide cylinder 1602 that was fluidically coupled to a pump 1604. The temperature and pressure conditions of the $CO_2$ were controlled using pressure controller 1606 and heater 1608. The pressure in the chamber 1620 was maintained by the pump 1604. An electrical heating blanket 1622 surrounded the chamber 1620 to maintain the temperature of the fluid in the chamber 1620 using temperature control module 1624. A collection vessel 1630 was fluidically coupled to the chamber 1620 through a pressure reduction valve 1625. The high-pressure stream of supercritical fluid plus solvent exits the top of the chamber 1620 and passes though the pressure reduction valve 1625 into the collection vessel where the solvent precipitates or condenses. The collection vessel 1625 may be cooled to facilitate removal of the solvent from the supercritical fluid stream. The supercritical fluid exits the collection vessel 1630 and passes through a rotameter 1640 and dry test meter 1642 to measure the volume of carbon dioxide used in the separation. The collection vessel 1630 was replaced with additional collection vessels during the trial run to collect different fractions.

EXAMPLE 2

A suitable supercritical fluid is one that is miscible with the solvent mixture, or at least one of the solvents in the solvent mixture, to be separated. At a certain pressure for a selected temperature the supercritical fluid can be miscible with the solvent mixture. A supercritical fluid can be selected such that phase separation of the solvent components in the supercritical fluid is achieved.

In the specific examples described below, the NMP/glycol samples exhibited phase separation when using carbon dioxide as a supercritical fluid. The pressure of the supercritical fluid used was 800-1000 psi and room temperature conditions were used.

EXAMPLE 3

The system described in Example 1 was used to separate NMP from a solvent mixture of about NMP and glycols in a waste water stream. The waste stream included a low solids amount of 1.2% with a matching water titration amount of 0.9% H2O by weight. The assay revealed both assorted glycols, most noticeably ethylene glycol, as well as NMP at 25% by weight and 75% by weight respectively. The above amounts were determined using gas chromatography.

The system of Example 1 and the conditions described in Example 2 were used to collect a series of fractions. The results are shown in Table 1 below. Five fractions of an NMP-rich phase were collected during the course of this test run. To aid in the collection of the NMP extract the collection flask was submerged in an acetone-dry ice bath during the course of this test.

TABLE 1

| Fraction | Wt (g) | Cumulative Wt % of Charge | Appearance |
| --- | --- | --- | --- |
| Feed | 102.0 | — | Dark Purple liquid |
| F1 | 4.0 | 3.9 | Dark Purple liquid |
| F2 | 15.6 | 19.2 | Dark Purple liquid |
| F3 | 11.9 | 30.9 | Dark Purple liquid |
| F4 | 25.7 | 56.0 | Dark Purple liquid |
| F5 | 14.7 | 70.5 | Dark Purple liquid |
| Raffinate | 24.5 | 24.0 | Blackish/brown liquid-different than feed and fractions |
| Total: | | 96.4 | 94.5 |

The results are consistent with total recovery of about 95% of the NMP from the solvent mixture with about 70.5 weight % NMP collected in the fractions and about 24 weight % of the glycols remaining the raffinate.

The system used was an open system, which likely leads to some loss of the NMP in the supercritical fluid stream exiting the collection vessel. A closed system, e.g., one where a recycle line is present, should lead to even larger amounts of recovery of the NMP from the waste stream.

When introducing elements of the aspects, embodiments and examples disclosed herein, the articles "a," "an," "the" and "said" are intended to mean that there are one or more of the elements. The terms "comprising," "including" and "having" are intended to be open-ended and mean that there may be additional elements other than the listed elements. It will be recognized by the person of ordinary skill in the art, given the benefit of this disclosure, that various components of the examples can be interchanged or substituted with various components in other examples.

Although certain aspects, examples and embodiments have been described above, it will be recognized by the person of ordinary skill in the art, given the benefit of this disclosure, that additions, substitutions, modifications, and alterations of the disclosed illustrative aspects, examples and embodiments are possible.

The invention claimed is:

1. A method of removing at least about 75% by weight or by volume of NMP, based on the total weight of a solvent mixture or based on the total volume of the solvent mixture respectively, from the solvent mixture comprising NMP and ethylene glycol in a chamber, the method comprising:

exposing the solvent mixture comprising the NMP and the ethylene glycol to a supercritical fluid stream of carbon dioxide at an effective temperature and pressure to remove at least about 75% by weight or by volume of the NMP, based on the total weight of the solvent mixture or based on the total volume of the solvent mixture respectively, from the solvent mixture comprising the NMP and ethylene glycol; and collecting the removed NMP in the supercritical fluid stream of carbon dioxide exiting the chamber.

2. The method of claim 1, comprising providing the supercritical fluid stream at an effective pressure to be miscible with the NMP.

3. The method of claim 1, further comprising depressurizing the removed NMP in the supercritical fluid stream to collect the removed NMP.

4. The method of claim 3, further comprising collecting the removed NMP in a closed vessel.

5. The method of claim 3, further comprising collecting the removed NMP in an open vessel.

6. The method of claim 1, further comprising recycling the supercritical fluid stream.

7. The method of claim 6, further comprising providing the recycled supercritical fluid stream to additional solvent mixture.

8. The method of claim 7, further comprising removing additional amounts of the NMP from the solvent mixture to remove a total of at least 99% by weight or by volume of the NMP from the solvent mixture.

9. The method of claim 6, exposing the collected NMP to the recycled supercritical fluid stream.

10. The method of claim 1, further comprising reusing the supercritical fluid stream to separate solvent mixture.

11. The method of claim 1, further comprising adding a carrier to the supercritical fluid stream to increase the amount of the NMP recovered compared to the amount of NMP recovered using the same supercritical fluid without the carrier.

12. The method of claim 1, further comprising detecting the NMP in the supercritical fluid stream.

13. The method of claim 1, further comprising drying the supercritical fluid after collecting the NMP.

14. The method of claim 13, further comprising providing the dried supercritical fluid back to the chamber.

15. The method of claim 1, further comprising configuring the supercritical fluid stream to be supercritical carbon dioxide at a pressure and temperature effective to be miscible with the NMP and the ethylene glycol.

* * * * *